(12) United States Patent
Kincaid et al.

(10) Patent No.: US 11,642,159 B2
(45) Date of Patent: May 9, 2023

(54) MEDICAL TOOL GUIDANCE APPARATUS

(71) Applicant: Canon U.S.A., Inc., Melville, NY (US)

(72) Inventors: Matthew Michael Kincaid, Medford, MA (US); Derek John Hugger, Mont Vernon, NH (US); Barret Daniels, Cambridge, MA (US); Takahisa Kato, Brookline, MA (US); Brian Ninni, Brighton, MA (US); John E. Longan, Nashua, NH (US)

(73) Assignee: Canon U.S.A., Inc., Melville, NY (US)

( * ) Notice: Subject to any disclaimer, the term of this patent is extended or adjusted under 35 U.S.C. 154(b) by 926 days.

(21) Appl. No.: 16/539,769

(22) Filed: Aug. 13, 2019

(65) Prior Publication Data

US 2020/0054378 A1 Feb. 20, 2020

Related U.S. Application Data

(60) Provisional application No. 62/875,243, filed on Jul. 17, 2019, provisional application No. 62/764,820, (Continued)

(51) Int. Cl.
*A61B 18/02* (2006.01)
*A61B 90/00* (2016.01)
(Continued)

(52) U.S. Cl.
CPC .............. *A61B 18/02* (2013.01); *A61B 6/032* (2013.01); *A61B 34/10* (2016.02); *A61B 90/06* (2016.02);
(Continued)

(58) Field of Classification Search
CPC . A61B 17/3403; A61B 17/3407; A61B 90/10; A61B 90/11
See application file for complete search history.

(56) References Cited

U.S. PATENT DOCUMENTS 4,608,977 A * 9/1986 Brown .................... A61B 90/11
378/162
5,163,430 A * 11/1992 Carol ..................... A61B 90/11
378/20

(Continued)

FOREIGN PATENT DOCUMENTS

CN 204797971 U 11/2015
JP 2012-515590 A 7/2012
(Continued)

*Primary Examiner* — Anu Ramana
(74) *Attorney, Agent, or Firm* — Canon U.S.A., Inc., IP Division

(57) ABSTRACT

A medical guidance apparatus (100) includes a base assembly (110) configured to be attached to a subject and a guide (150) configured to be removably mated with the base assembly (110). The base assembly (110) has an opening (160), and the guide (150) includes a rotatable ring (152) and an arc member (154). The arc member (154) includes a first end (162) and a second end (164), the first end of the arc member is connected to the rotatable ring (152) and the second end extends diametrically opposite to the first end across the rotatable ring. A probe holder (600) is mounted on the arc member (154) so as to hold a needle-like instrument (2161) at a desired angle relative to an axis (Ax) of the rotatable ring (152). In some embodiments, the arc member is monolithically integrated with the rotatable ring. In other embodiments, the arc member is pivotable and/or completely removable from the rotating ring.

29 Claims, 19 Drawing Sheets

Related U.S. Application Data filed on Aug. 15, 2018, provisional application No. 62/764,849, filed on Aug. 15, 2018.

(51) Int. Cl.

| | | |
|---|---|---|
| *A61B 34/10* | (2016.01) | |
| *A61B 6/03* | (2006.01) | |
| *A61B 90/11* | (2016.01) | |
| A61B 18/00 | (2006.01) | |
| A61B 17/00 | (2006.01) | |
| A61B 17/34 | (2006.01) | |

(52) U.S. Cl.
CPC .............. *A61B 90/11* (2016.02); *A61B 90/39* (2016.02); *A61B 2017/00128* (2013.01); *A61B 2017/3407* (2013.01); *A61B 2018/00577* (2013.01); *A61B 2018/0293* (2013.01); *A61B 2034/107* (2016.02); *A61B 2090/067* (2016.02); *A61B 2090/3966* (2016.02)

(56) References Cited

U.S. PATENT DOCUMENTS

| | | |
|---|---|---|
| 5,196,019 A | 3/1993 | Davis et al. |
| 5,201,742 A | 4/1993 | Hasson |
| 6,487,431 B1 | 11/2002 | Iwano et al. |
| 6,505,065 B1 | 1/2003 | Yanof et al. |
| 7,824,417 B2 | 11/2010 | Magnusson et al. |
| 8,511,316 B2 | 8/2013 | Boese et al. |
| 9,125,676 B2 | 9/2015 | Sahni |
| 9,192,446 B2 | 11/2015 | Piferi et al. |
| 9,222,996 B2 | 12/2015 | Fujimoto et al. |
| 9,408,627 B2 | 8/2016 | Sahni |
| 9,433,390 B2 | 9/2016 | Nathaniel et al. |
| 9,867,673 B2 | 1/2018 | Onuma et al. |
| 2004/0260312 A1 | 12/2004 | Magnusson et al. |
| 2006/0229641 A1 | 10/2006 | Gupta et al. |
| 2008/0200798 A1 | 8/2008 | Eklund et al. |
| 2010/0063496 A1 | 3/2010 | Frovato et al. |
| 2010/0082040 A1 | 4/2010 | Sahni |
| 2011/0190787 A1 | 8/2011 | Sahni |
| 2012/0022368 A1 | 1/2012 | Brabrand et al. |
| 2014/0022245 A1 | 1/2014 | Brannan et al. |
| 2016/0038247 A1 | 2/2016 | Bharadwaj et al. |
| 2017/0014200 A1 | 1/2017 | Onuma et al. |
| 2018/0228568 A1 | 8/2018 | Kato et al. |
| 2019/0105109 A1 | 8/2019 | Kato |

FOREIGN PATENT DOCUMENTS

| | | |
|---|---|---|
| JP | 2015-047303 A | 3/2015 |
| WO | 2010/096149 A2 | 8/2010 |

* cited by examiner

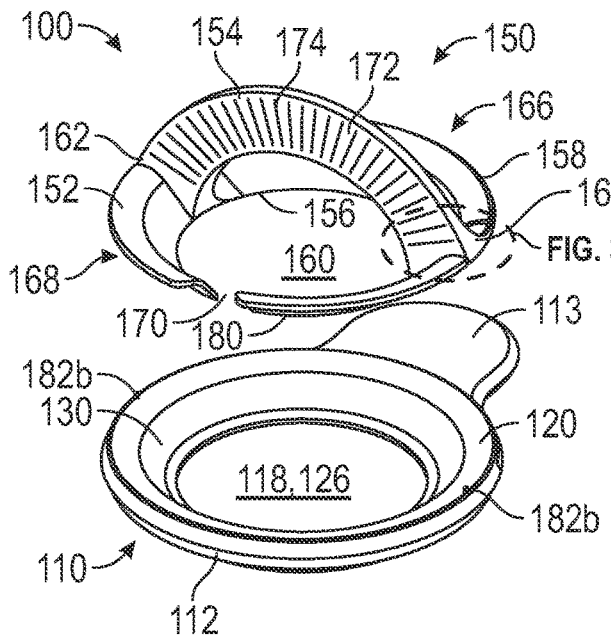
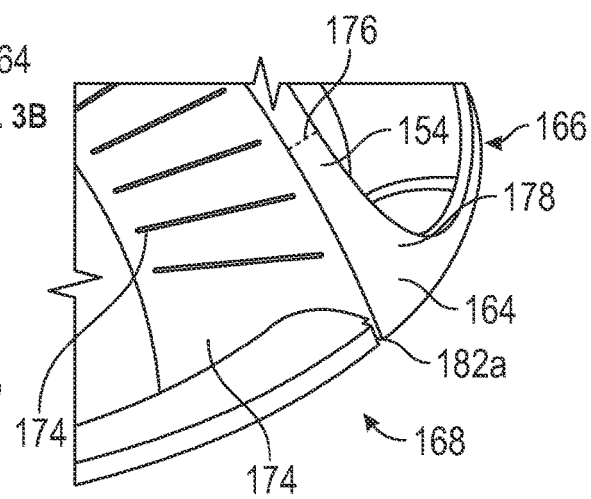
FIG. 3A  FIG. 3B
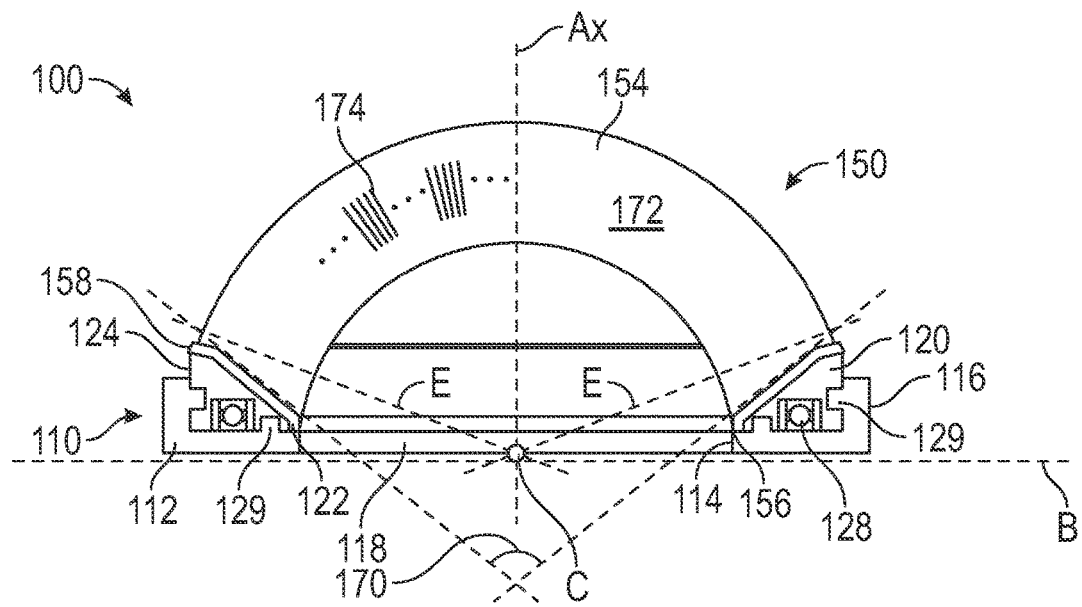
FIG. 4

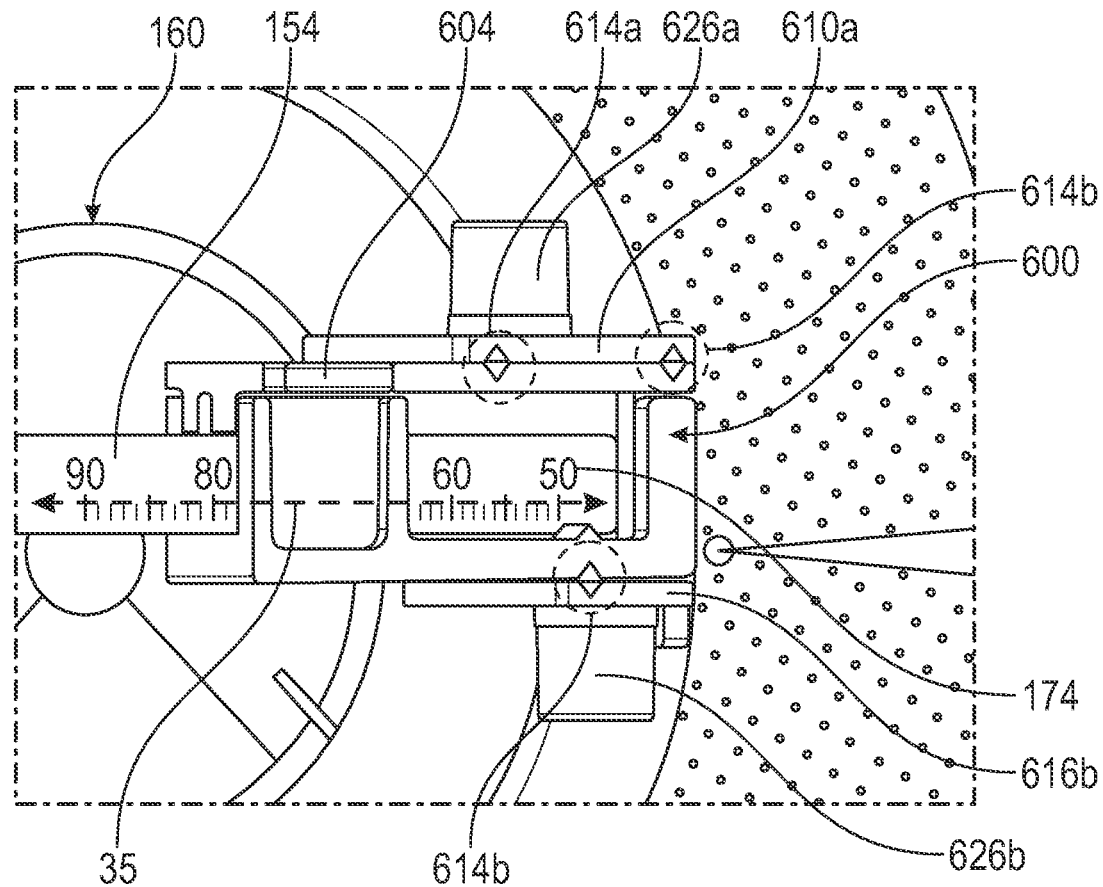
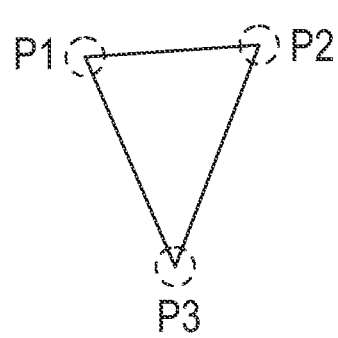
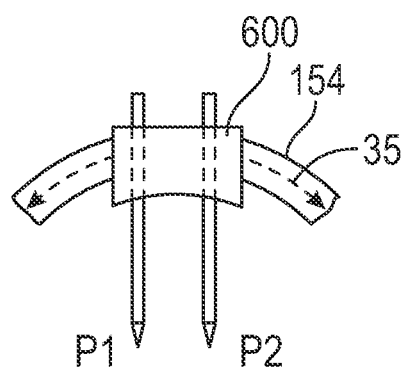
FIG. 28A
FIG. 28B
FIG. 28C

MEDICAL TOOL GUIDANCE APPARATUS

CROSS-REFERENCE TO RELATED APPLICATIONS

The present application claims priority to U.S. provisional application 62/875,243 filed Jul. 17, 2019, and U.S. provisional application 62/764,820 and U.S. provisional application 62/764,849, both filed Aug. 15, 2018. The disclosures of the above-referenced provisional applications are incorporated by reference herein in their entirety.

FIELD OF THE DISCLOSURE

The present disclosure relates generally to medical devices, and in particular it relates to medical guidance apparatuses for holding and positioning one or more medical instruments, and more particularly, to an apparatus suitable for minimally invasive puncture treatment.

BACKGROUND OF THE DISCLOSURE

Percutaneous puncture treatment, in which a medical instrument, such as a needle, is guided to the affected part, is a typical example of minimally invasive treatment that is commonly performed. Examples of puncture treatments include ablation treatment in which a tumor or cancer cells are burned with radio waves and cryotherapy in which a tumor or cancer cells are frozen by using, for example, a freezing device or cooling gas. Puncture biopsy has also been commonly performed in pathological diagnosis based on tissue sampling.

In the medical environment, it is necessary to position a needle or multiple needles precisely inside tissue or a specific organ for accurate diagnosis or minimal invasive therapy. Biopsy, ablation, cryotherapy, aspiration and drug delivery are examples that require high precision needle placement and many of these treatments require the use of multiple needles in a treatment. To achieve accurate and intuitive orientation of medical tools such as needle-like puncture instruments, and to reduce dependency of the outcome on the user's skills, different systems and methodologies have been disclosed. Pictures (images) are used to direct these procedures, which are usually done with needles or small catheters that are inserted into the body of a patient through the skin or through a body cavity or anatomical opening. The images allow physicians to safely guide these instruments through the body to the target areas of interest.

Prior to a percutaneous incision, a target area of interest (e.g., tumor, nodule, etc.) is confirmed by means of non-invasive imaging with magnetic resonance imaging (MRI), computed tomography (CT), ultrasound or other imaging modality. Once the target area of interest is positively determined, the clinician decides an entry point, an inserting direction, and depth to be reached by the needle. This process often requires a lengthy trial and error routine, which can be deleterious to the patient. Accordingly, in the last few decades there has been an increased interest in the development of needle guiding systems that can improve accuracy of needle positioning, minimize patient discomfort, and shorten time of operation.

To accurately position a needle with respect to a target, such as a tumor, in puncture treatment, an X-ray computed tomography (CT) unit, an MRI unit, etc., for acquiring medical images is used as a visualization unit for visualizing the needle. In puncture treatment in which such a modality is used as a visualization unit, it is often difficult to position the needle with respect to the target are by a single puncturing process. Thus, the needle is generally guided to the target by acquiring medical images multiple times and correcting the insertion trajectory little by little in accordance with information from the acquired images. Accordingly, to reduce the operation time and burden on patients as well as patient's exposure to imaging radiation, various needle positioning apparatuses for positioning the needle to the target to provide a reduction in the number of times of corrections of the trajectory have been developed.

For example, U.S. Pat. Nos. 9,125,676 and 9,408,627 discloses a needle positioning apparatus having a cantilever arc guide structures with two ends attached to a base or support ring such that the guides are compliant against induced forces on both of the ends. The guides may experience large deformation forces during assembly. This assembly error in turn causes position inaccuracy. Furthermore, the guides have relatively low stiffness and do not maintain a precise position when subjected to force from the medical tool during guidance. Additionally, with respect to the apparatus of U.S. Pat. No. 9,125,676, a locking pin is used to maintain the arc guide perpendicular to the base plate. This causes large angle error because the fixing position is close to the triangle vertex of the angle, which increases an angular error with the small position error. Even when the locking pin is unlocked, the arc guide is free to rotate in an incorrect angular direction. Thus, whether locked or unlocked there is a large angular error. Finally, the base plate of the U.S. Pat. No. 9,125,676 apparatus exposes the bearing surface for the arc guide to the external environment, which risks dust and fluid to enter during a medical procedure. Pre-grant patent application publication US 2008/0200798 also discloses a medical device trajectory guide where a guide tube is attached to a base plate which is attached or placed directly over the desired target tissue. The trajectory guide is freely angularly movable relative to the base and can be aligned with the desired tissue site. Other examples of guidance devices for medical needle-like instruments include pre-grant publication US 2012/0022368, and U.S. Pat. Nos. 4,608,977, 5,201,742, and 7,824,417.

The existing art suffers from particular drawbacks which limit stability during the use of such medical devices, and reduce visibility and access to the insertion area of interest. All related devices disclose guiding a needle or needle-like instrument along a trajectory. The primary purpose of these devices is to establish the orientation at which to insert a needle/probe/instrument, and to help the physician maintain this orientation as insertion occurs. However, during needle insertion, forces are generated due to resistance to probe insertion from the anatomy of the patient or due to patient movement (e.g., due to breathing or organ displacement). These forces can be transmitted to the guide device and if the guide device is not designed in such a way that these forces can be counteracted, the trajectory can be altered.

This is particularly true in devices where the arc guide attaches to the base through small base support sections which does not provide enough stiffness to resist such forces. In U.S. Pat. Nos. 9,408,627 and 9,125,676, for example, both devices have a cantilevered arc connected to the rotating base through small base support sections. In this case, the small size of the base support sections has limited ability to resist momentum forces experienced by the arc during needle insertion. Other devices are fabricated from thin plastic pieces, and thus also lack of stiffness to counter unexpected forces. In these devices, due to the weight of the needle/catheter/probe, especially the weight of the portion of the needle which is outside the body, gravity will deflect the needle from its intended path.

Moreover, guidance devices are an aid during an interventional procedure, be it a biopsy, drainage, ablation, or the like. In any procedure, the physician typically needs access to the surgical area to make incisions, apply saline fluid, stabilize the skin surface with their fingers, etc. Therefore, access and visibility to the insertion region are important such that the physician can use the guidance device without disrupting the procedure, but also ensuring patient safety. To provide access and visibility to the insertion site, the guidance device must have a sizable aperture around the insertion site, both on the skin surface and above it. However, most known guide devices do not provide physician access to the insertion area of interest. In this regard, the ability of the guide device to be moved out of the site of insertion procedure (as disclosed in publication US 2012/0022368) may add convenience. However, in the event where multiple insertions are required, the removal of the guide device would disrupt the procedure because the guide device may not be repositioned in the exact same location, or, in the case of image guided interventions, it would be necessary to repeat the registration of the guide device with the patient.

Therefore, there remains a need in the industry to further refine and advance the technology to address the above-referenced difficulties.

SUMMARY

Thus, to address such exemplary needs in the industry, the disclosure teaches a medical guidance apparatus which includes a base assembly configured to be attached to a subject and a guide configured to be removably mated with the base assembly. The base assembly has an inner circumference defining an opening, and the guide includes a rotatable ring and an arc member. In a configuration where the guide is mated with the base assembly, the opening of the rotatable ring overlays the opening of the base assembly. The arc member has as a first end and a second end, the first end of the arc member is connected to the rotatable ring and the second end extends diametrically opposite to the first end across the rotatable ring. A probe holder is mounted on the arc member so as to hold a needle-like instrument at a desired angle relative to an axis of the rotatable ring.

According to one embodiment, a medical guidance apparatus comprises: a base assembly including a base ring having an inner circumference defining an opening, and a guide rotateably mateable with the base assembly, the guide having a frame ring with an inner circumference defining an opening and an outer circumference, wherein, in a configuration where the guide is mated with the base assembly, the opening of the frame ring overlays the opening of the base ring. The medical guidance apparatus also has an arc member and a holder slideably attached to the arc member, wherein the holder is configured to hold a medical tool intended to be guided by the medical guidance apparatus.

In various embodiments of the subject disclosure, the medical guidance apparatus has an arc member which is hingedly attached to the frame ring. In yet additional embodiments, the arc member comprises a guidance surface, wherein the guidance surface comprises one or more angular reference marks. The angular reference marks are intended to align with an indicator configured upon the arc member guidance surface to accurately situate the holder in the desired angular position.

In various embodiments, the indicator comprises a magnifier for magnification of the arc member guidance surface.

In further embodiments, the medical guidance apparatus comprises a gap extending from the inner circumference of the frame ring to the outer circumference of the frame ring, to allow for detachment and/or reattachment of the medical guidance apparatus to the surface without interrupting the medical tool.

In other contemplated embodiments, the holder is affixed to the arc member by a locking lever. In additional embodiments, the holder further comprises a groove for accepting the medical tool and a door for holding the medical tool in the holder. Furthermore, the door may be hingedly attached to the holder, and further comprises a tab, configured to align with the groove on the holder, to aid in holding the medical tool in the holder. In other embodiments, the door may be removable and/or replaceable.

In another embodiment of the subject disclosure, the medical guidance apparatus further comprises a second groove for accepting a second medical tool, wherein the door further comprises a second tab configured to align with the second groove to aid in holding the second medical tool in the holder. It is further contemplated that the medical guidance apparatus further comprises a controller box in electrical communication with the base ring.

In another embodiment, the medical guidance apparatus further comprises an adhesive marker attached to an underside surface of the base assembly, wherein the adhesive marker comprises a backing material and an adhesive extending across an underside surface of the backing material. Furthermore, the backing material comprises a peel-away portion aligned with the opening of the base ring. In addition, the adhesive marker may further comprise a center marker disposed on the peel-away portion, wherein the center marker indicates the center point of the opening of the base ring.

In further embodiments, the arc member comprises a first arc component and a second arc component, wherein the first arc component is spaced apart from and opposed to the second arc component.

The present disclosure further discloses a medical guidance apparatus comprising a base ring having an inner circumference defining an opening, a moveable ring having an inner circumference defining an opening, the moveable ring being rotateably coupled with the base ring, a rotary encoder; and a guide mateable with the moveable ring, wherein the guide includes a frame ring having an inner circumference defining an opening and an outer circumference. The apparatus also includes an arc member and a holder slideably attached to the arc member, wherein the holder is configured to hold a medical tool intended to be guided by the medical guidance apparatus, wherein, in a configuration where the guide is mated with the moveable ring, the opening of the frame ring overlays the opening of the base ring and the opening of the moveable ring, and wherein the encoder is configured to measure an angular position of the moveable ring.

Further embodiments of the subject disclosure includes a method of guiding a medical instrument, comprising, mounting a medical guidance apparatus about a predetermined insertion point of a surface, the medical guidance apparatus comprising a base assembly including a base ring having an inner circumference defining an opening and a guide rotateably mateable with the base assembly, the guide including a frame ring having an inner circumference defining an opening and an outer circumference, wherein, in a configuration where the guide is mated with the base assembly, the opening of the frame ring overlays the opening of the base ring. The apparatus further boasting an arc member and a holder slideably attached to the arc member, wherein the holder is configured to hold a medical tool intended to be guided by the medical guidance apparatus. The method further comprises, positioning the guide to a predetermined position relative to the base ring, positioning the medical instrument to a predetermined position upon the holder, and inserting the medical instrument through the insertion point.

According to at least one embodiment of the disclosure, there is provided a medical guide device for a puncture instrument having improved stability and access. In one embodiment, the guide device comprises a base plate, a rotatable ring, an arc shaped guide, and a probe holder. The base plate has top and bottom surfaces and an opening connecting the top and bottom surfaces; the rotatable ring is attached to the top surface of the base plate; a first end of the arc shaped guide is pivotably hinged to a first section of the rotatable ring and a second end of the arc shaped guide is releasably clipped to a second section diametrically opposite to the first section of the rotatable ring. The probe holder is mounted on the arc shaped guide so as to hold a needle-like instrument at a desired angle relative to the base plate. During an interventional procedure, the arc shaped guide can be pivoted relative to the rotatable ring away from an insertion path and/or it can be entirely removed from the rotatable ring.

According to an embodiment, a guide apparatus is configured to guide a medical needle-like instrument for use in an image guided intervention procedure. The guide apparatus is composed of a base which has a circular opening, a rotating ring arranged on the base, an arc, and a probe holder. The rotating ring can be fixed in a position to the base using a cam latch mechanism. The arc is hinged on a first end and is clipped-in on the second end to the ring. The hinged end includes a c-shaped hinge that can be clipped-in onto a cylindrical pin, so the arc can be fully removed if necessary. The probe holder slides along the arc and can be fixed at any location along the arc using a cam latch mechanism. In one embodiment, the circular opening of the base is approximately 50 millimeters (mm) in diameter, and the aperture underneath the arc, when the arc is closed, is about 50 mm as well. The hinged end of the arc can be pivoted relative to the rotatable ring so that the arc and probe holder can move away from an insertion path. If necessary, the arc can be entirely removed from the rotatable ring. This allows improved accessibility and visibility of an area of interest.

These and other objects, features, and advantages of the present disclosure will become apparent upon reading the following detailed description of exemplary embodiments of the present disclosure, when taken in conjunction with the appended drawings.

BRIEF DESCRIPTION OF THE DRAWINGS

FIG. 3A is a partial exploded perspective view of the medical guidance apparatus illustrated in FIG. 1. FIG. 3B is a close-up perspective view of a portion of the medical guidance apparatus illustrated in FIG. 3A.

FIG. 4 is a cross-sectional view of the medical guidance apparatus taken along line 4-4 of FIG. 2.

FIGS. 28A 28B, through 28C show an embodiment of a probe holder 600 configured for multi-probe use.

Figure 1:
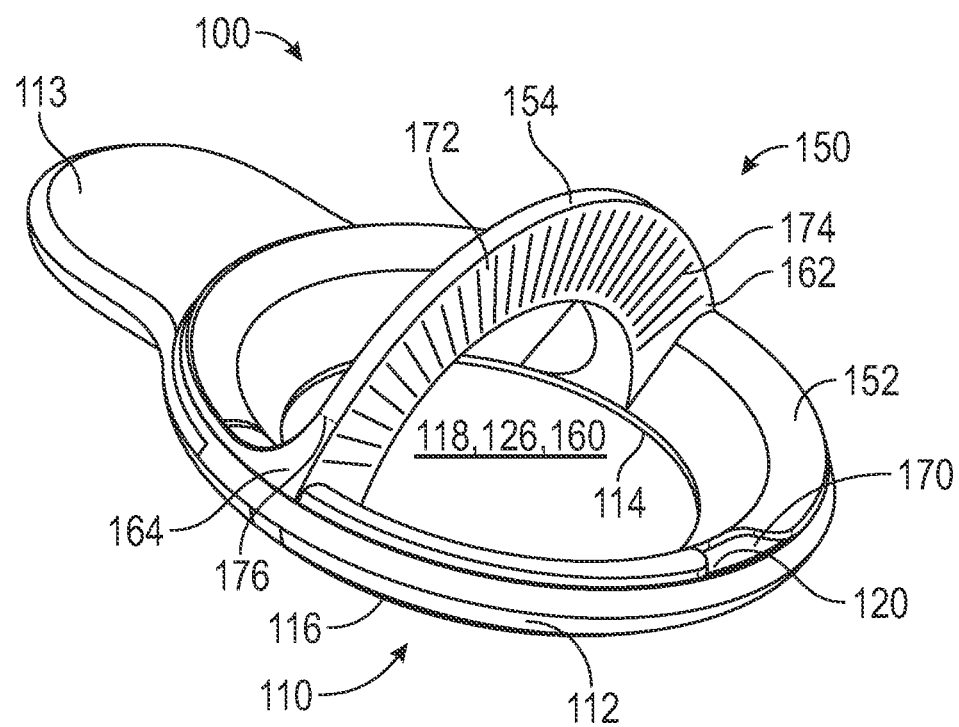
FIG. 1 is a perspective view of an example medical guidance apparatus 100 in accordance with various aspects of the disclosure.

Throughout the Figures, the same reference numerals and characters, unless otherwise stated, are used to denote like features, elements, components or portions of the illustrated embodiments. In addition, reference numeral(s) including by the designation of prime "'" (e.g. 12' or 24') signify secondary elements and/or references of the same nature and/or kind. Moreover, while the subject disclosure is described in detail with reference to the enclosed Figures, it is done so in connection with the illustrative embodiments. It is intended that changes and modifications can be made to the described embodiments without departing from the true scope and spirit of the subject disclosure as defined by the appended claims.

DETAILED DESCRIPTION OF THE DISCLOSURE

In referring to the description, specific details are set forth in order to provide a thorough understanding of the examples disclosed. In other instances, well-known methods, procedures, components and materials have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description and/or illustration to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. The term "position" or "positioning" should be understood as including both spatial position and angular orientation.

Some embodiments of the present disclosure may be practiced in conjunction with a computer system that includes, in general, one or a plurality of processors for processing information and instructions, RAM, for storing information and instructions, ROM, for storing static information and instructions, a data storage device such as a magnetic or optical disk and disk drive for storing information and instructions, (e.g., an MRI image) an optional user output device such as a display device (e.g., a monitor) for displaying information to the computer user, and an optional user input device.

As will be appreciated by those skilled in the art, some aspects of the disclosure may be embodied, at least in part, as a computer program product embodied in any tangible medium of expression having computer-usable program code stored therein. For example, some aspects described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram.

In the following description, reference is made to the accompanying drawings which are illustrations of exemplary embodiments. It is to be understood, however, that those skilled in the art may develop other structural and functional modifications without departing from the novelty and scope of the instant disclosure.

Figure 2:
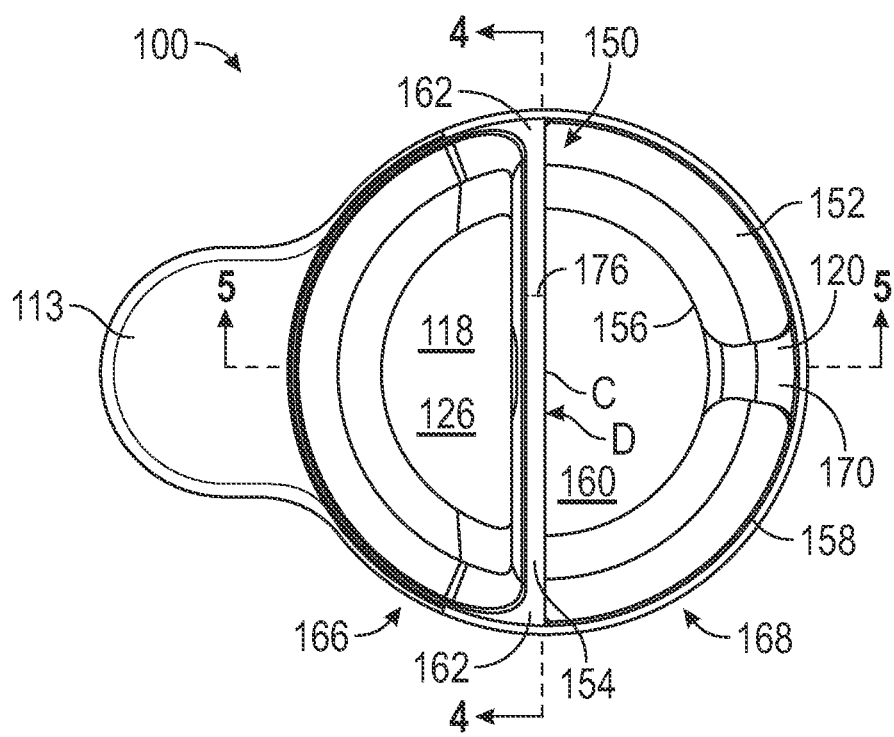
FIG. 2 is a top view of the medical guidance apparatus illustrated in FIG. 1.
Figure 5:
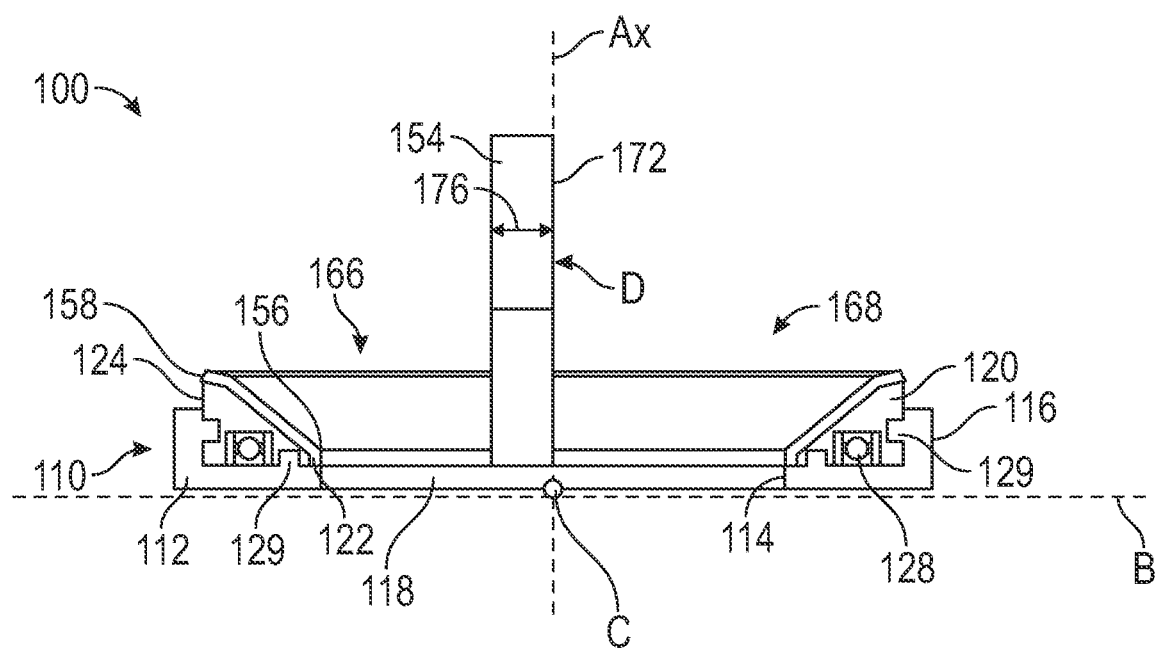
FIG. 5 is a cross sectional view of the medical guidance apparatus taken along line 5-5 of FIG. 2.

FIG. 1 is a perspective view of a medical guidance apparatus 100 according to an example embodiment. FIG. 2 is top view of the medical guidance apparatus 100. FIG. 3A is a partially exploded view of the medical guidance apparatus 100. FIG. 4 is a cross sectional view taken along line 4-4 of FIG. 2, and FIG. 5 is a cross sectional view taken along line 5-5 of FIG. 2. The medical guidance apparatus 100 may generally include a base assembly (base) 110 and a guide 150. The guide 150 is configured to be coupled, mated, or otherwise mechanically engaged with the base assembly 110. Further, in its engaged state, the guide 150 is configured to be movable in a circular path, rotatable, or otherwise turn, revolve or spin with respect to the base assembly 110. FIGS. 1 and 2 illustrate the guide 150 coupled with the base assembly 110 (a coupled or engaged state). Accordingly, the guide 150 can also be decoupled, disengaged, or otherwise removed from the base assembly 110. FIG. 3 illustrates the guide 150 removed from the base assembly 110 (a removed, decoupled, or disengaged state). Further description of the guide 150 and the manner in which the guide 150 is coupled with the base assembly 110 is described in more detail below.

As shown in the various figures, the base assembly 110 includes a base ring 112 in the form a ring shape having an inner circumference 114 and an outer circumference 116 (see FIGS. 1, 4 and 5). The inner circumference 114 defines an opening 118. The opening 118 provides access to the patient when the medical guidance apparatus 100 is mounted onto a patient. That is, the opening 118 provides an area in which the patient's skin is exposed and accessible. The base ring 112 may also be referred to as a "fixed ring" or "stationary ring" because the base ring 112 is affixable to the patient and is not rotatable once affixed to the patient. The width of the base ring 112 (i.e., the distance from the inner circumference 114 to the outer circumference 116 in a radial direction, which is also the difference between the inner radius and the outer radius of the base ring 112), may be ⅙ to ½, more preferably ¼ to ⅓, the diameter of the opening 118. In one example, the outer diameter of the base ring 112 may be from 50 to 150 mm (for example 80 mm) and the inner diameter (i.e., the diameter of the opening 118) may be 30 mm to 110 mm (for example 60 mm).

The base assembly 110 further includes a moveable ring 120. The moveable ring 120 is best seen in FIGS. 3A, 4, and 5. The moveable ring 120 may be in the form of a ring shape having an inner circumference 122 and an outer circumference 124. The inner circumference 122 defines an opening 126 that also provides access to the patient. The width of the moveable ring 120 (i.e., the distance from the inner circumference 122 to the outer circumference 124 in a radial direction, which is also the difference between the inner radius and the outer radius of the moveable ring 120), may be ⅙ to ½, more preferably ¼ to ⅓, the diameter of the opening 126. In one example, the outer diameter of the moveable ring 120 may be from 50 to 150 mm (for example 75 mm) and the inner diameter (i.e., the diameter of the opening 126) may be 30 mm to 110 mm (for example 65 mm). The moveable ring 120 may also be referred herein as a "rotatable ring" of the base assembly because the moveable ring 120 is capable of rotating about an axis Ax passing through a center point C. The center point C is the center of the circular opening 126 defined by the inner circumference 122. The axis Ax extends vertically through the center point C, i.e., perpendicularly relative to a horizontal plane B defining the surface to which the base assembly 110 may be mounted (see, e.g., FIGS. 4 and 5).

The moveable ring 120 may rotate, turn, or otherwise move relative to the base ring 112 via a bearing 128, as best seen in FIGS. 4 and 5. Thus, the base ring 112 may be referred to as a fixed ring because it is not rotatable, while the moveable ring 120 may be referred to as rotatable ring because it is rotatable relative to the base ring 112 via the bearing 128. The bearing 128 may be a ball bearing or any other suitable bearing structure known in the art that allows for relative motion between two concentric rings. For example, the bearing 128 may be a plain bearing, a roller bearing, and the like. As shown in FIGS. 4 and 5, the base assembly 110 may further include a seal 129. The seal 129 protects the bearing 128 by preventing contamination from the external environment from coming into contact with the bearing 128.

The base assembly 110 may further include a handle or grip 113. The grip 113 may be attached to or integral with the base ring 112. The grip provides a mechanism for the operator to grasp the base assembly 110 and increase stability of the base assembly 110 during insertion of a medical instrument. Additionally, the grip 113 may house electronic components related to the use of LED arrays, which is discussed below with respect to FIG. 9. The grip 113 may also include visible markers or other type of indicators.

The guide 150 comprises a frame ring 152 and an arc member 154. The frame ring 152 may have a ring shape similar to the base ring 112 and the moveable ring 124. Therefore, the frame ring 152 has an inner circumference 156 and an outer circumference 158. The inner circumference 156 defines an opening 160. The opening 160 is concentric with the opening 118 and opening 126, and it provides access to the patient. The width of the ring shape of the frame ring 152 (i.e., the distance from the inner circumference 156 to the outer circumference 158 in a radial direction, which is also the difference between the inner radius and the outer radius of the frame ring 152), may be ⅙ to ½, more preferably ¼ to ⅓, the diameter of the opening. In one example, the outer diameter of the frame ring 152 may be from 50 mm to 150 mm (for example 75 mm) and the inner diameter (i.e., the diameter of the opening 160) may be 30 mm to 110 mm (for example 65 mm).

As shown in FIGS. 1 and 3A, the arc member 154 may include a first end 162 and a second end 164. Each of the ends 162 and 164 may connect to the frame ring 152 on diametrically opposed sides of the frame ring 152, thereby bisecting the frame ring 152 in a first half 166 and a second half 168 (best seen in FIG. 2). In various embodiments, the arc member 154 may be hinged at a first end 162 for pivotal attachment to the frame ring 152, with a fastener at the second end 164, such that the arc member 154 may be pivoted. In other embodiments, the second end 164 may be affixed to the frame ring 152 by a locking device or other fastener intended to removably affix the arc member 154 to the frame ring 152. In yet additional embodiments, the arc member 154 may be removably attached to the frame ring 152 at both the first end 162 and the second end 164, thus allowing for complete removal of the arc member 154. The first end 162 and second end 164 may be affixed to the frame ring 152 by a locking device or other fastener (e.g. pin, R-clip, spring-clip) intended to removably affix the arc member 154 to the frame ring 152. It is further contemplated that the arc member 154 may be slideably attached to the frame ring 152 at the first end 162 and/or second end 164 to facilitate easy removal and reattachment of the arc member 154 to the frame ring 152.

The frame ring 152 may be continuous circular structure or may include a gap 170 such that the second half 168 of the frame ring 152 is non-continuous. That is, the gap 170 serves as an interruption in the second half 168 of the frame ring 152. The gap 170 may be sized such that a medical instrument may pass through the gap 170 into opening 160 of the frame ring 152. The medical instrument can be an ablation probe in cryoablation, microwave ablation, radiofrequency ablation, laser ablation and irreversible electroporation ablation. Also, the medical instrument can be a needle-like device, for example biopsy needle, aspiration needle and drainage needle. The gap 170 has a width wide enough to get the medial instrument through for inserting and releasing. In other words, the gap 170 may extend from the inner circumference 156 to the outer circumference 158 of the frame ring 152 to provide a pathway for in instrument to exit the frame ring 152, as will be discussed below in more detail. The gap 170 may extend radially relative to the center of the opening 160 through the frame ring 152. The gap 170 may also extend non-radially (i.e., curved or spiral relative to the center of the opening 160). The first half 166 of the frame ring 152 may be continuous and lacking any gap. That is, from the point on the frame ring 152 where the first end 162 of the arc member 154 meets the frame ring 152 to the point on the frame ring 152 where the second end 164 of the arc member 154 meets the frame ring 152, the frame ring 152 is a continuous structure. In other words, the first half 166 of the frame ring 152 has a closed structure while the second half 168 of the frame ring 152 has a non-closed/ open or interrupted structure.

The arc member 154 has an arc shape that spans an angle 170 relative to the horizontal plane B (see FIG. 4). The angle 170 may be from 60 to 170 degrees, more preferably from 120 to 150 degrees. The arc member 154 may include a guide surface 172 that provides a guidance area for the instrument. The arc member 153 may include a plurality of angular reference marks 174 on the guide surface 172. The guide surface 172 may have a different color than the color of the surface on the opposite side of the arc member 154 (see also FIGS. 9 and 10). Having a different color allows the operator to quickly and easily ascertain which surface is the guide surface. This is particularly useful in an embodiment lacks the plurality of reference marks, as discussed below. The angular reference marks 174 signify an angle around center point C.

The use of the angular reference marks 174 is described below as part of a method of guiding a medical instrument. The angular reference marks 174 may be visible optically as well as in CT and X-ray images utilizing radio-opaque material. The radio-opaque material can be, but is not limited to, plastic including fillers of barium sulfate, bismuth subcarbonate, bismuth oxychloride, tungsten, and the like. As shown in FIG. 3B, the arc member 154 may have a thickness 176. The thickness 176 may be $\frac{1}{15}$ to $\frac{1}{3}$ the diameter of the opening 160, more preferably $\frac{1}{12}$ to $\frac{1}{5}$ the diameter of the opening 160, more preferably $\frac{1}{10}$ to $\frac{1}{5}$ the diameter of the opening 160. In various embodiments, the angular reference marks 174 may be provided on at least one side of the arc member 154, as shown in FIG. 3B. However, the angular reference marks 174 may also be provided on the thickness 176 portion of the arc member 154, thus allowing for viewing of the angle from a top perspective. The angular reference marks 174 may be presented in any desired increment and/or scale, with various increments being sized differently for indication purposes.

The ends 162 and 164 of the arc member 154 may be integrally formed with the frame ring 152 such that the entire guide 150 is monolithically formed. That is, the entire guide 150 may be cast as a single piece of material. Additionally, as shown in FIG. 3B, each of the ends 162 and 164 may include a fillet structure 178 on the side of the arc member 153 that transitions to the closed first half 166.

In some embodiments, the plurality of angular reference marks 174 on the guide surface 172 may comprise LED indicators. These LED indicators provide illumination of the guide surface or they may be turned on to indicate, for example, an angle of planned entry (e.g., a red lit indicator appears at the planned entry angle). For a medical guidance apparatus that is configured to detect the angle of a needle positioned in or near the medical guidance apparatus, the LED may be used to display when the needle is approaching or at a 'correct angle' by, for example, signaling with a green lit indicator at that angle. That is, a red lit indicator appears at the planned entry angle and green lit indicator appears when the needle-like instrument is approaching-to or at the correct angle.

Each of the monolithic structure of the guide 150, the closed structure of the first half 166 of the frame ring 152, the thickness 176 of the arc member 154, and the fillet structure 178 contributes to a structural advantage as compared to prior art devices. In particular, when a force is applied to arc member 154 in a direction D against the guide surface 172 (see FIGS. 2 and 5), these structural features provide sufficient stiffness and rigidity to provide support and to minimize deflection, thereby providing sufficient support for positioning and driving the needle-like instrument. This structure provides a high rigidity while the structure still provides an opening for needle egress. This is in contrast to a cantilever shape, i.e. an open frame, the monolithic structure has a greater stiffness and can withstand the forces associated with needle placement and maneuvering with smaller deflection. Further, the stiffness of the closed first half 166 can be improved by increasing thickness of the closed first half while keeping the gap 170 in the second half 168.

Additionally, because of the monolithic structure, assembly error can be avoided. The structure of the guide 150 is able to provide this structural support despite having the gap 170 in the second half 168.

As best seen in FIG. 3A, the base assembly 110 and the guide 150 may each include corresponding tapered (or angled) portions 130 and 180, respectively. The taper portion 130 of the base assembly 110 may be formed as part of the moveable ring 120 and may extend around the entire circumference of the moveable ring 120. The taper portion 180 of the guide 150 may be formed along the entire circumference of the frame ring 152. The two tapered portions 130 and 180 may be congruently formed such that tapered portion 180 of the guide 150 geometrically fits within the tapered portion 130 of the base assembly 110. By having a congruent geometry, guide 150 may easily mate with the base assembly 110 via the tapered portions 130 and 180. In addition to allowing for easier mating, the tapered portions provide greater range of angles for the angular reference marks 174 than as compared to a non-tapered configuration. Furthermore, the taper feature increases the structural rigidity of the arc member 154 against the force of the medical instrument imparted on the arc member 154 during guidance.

In another aspect, when no moveable ring 120 is present (discussed below), the tapered portion 130 of the base assembly 110 may instead be formed directly in the base ring 112. In such an arrangement, the tapered portion 180 of guide 150 is geometrically congruent with a taper portion 130 of the base ring 112 in the same manner that the taper portion 180 may be geometrically congruent with the taper portion 130 of the moveable ring 120. In other words, the taper portions may be used to directly frictionally mate the guide 150 with the base ring 112. The angle or amount of taper in the tapered portion 180 is exemplified in FIG. 4, as angle 170. However, the specific angle of the taper is not limiting. In some embodiments, the taper portions of the base assembly and taper portions 130 and 180 can be understood as a conical interface, where the base assembly 110 and guide 150 are geometrically aligned at the taper portions 130 and 180 to the center axis of the conical interface. Kinematically, the tapered interface eliminates in-plane relative motion between the base assembly 110 and guide 150, while allowing the guide 150 to rotate around axis Ax without tilting.

Figure 6:
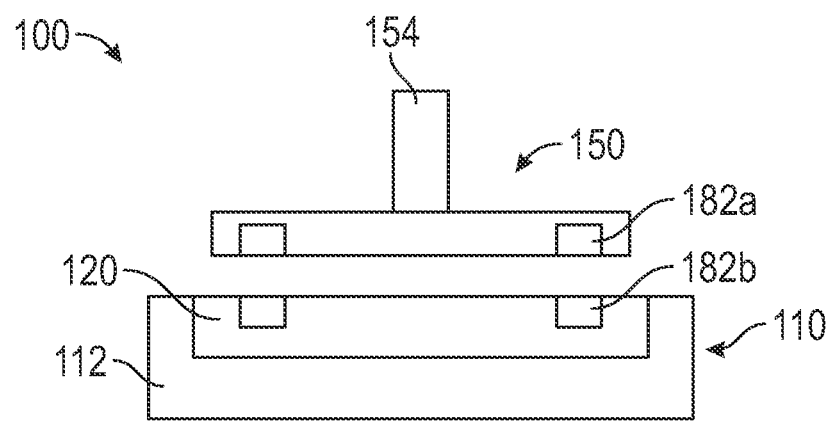
FIG. 6 is a schematic cross section of the medical guidance apparatus illustrated in FIG. 1.

As noted above the guide 150 may be rotatably coupled with the base assembly 110 via a tapered structure. In one aspect, this may be achieved by mechanically coupling the frame ring 152 of the guide 150 to the moveable ring 120 via a mechanical interface. FIG. 6 illustrates a schematic cross-sectional representation of the principle of mechanically mating the guide 150 with the base assembly 110. As shown in FIG. 6, the guide 150 may include a first mechanical component 182a and the moveable ring 120 may include a second mechanical component 182b. The first and second mechanical components 182a and 182b together are the mechanical interface that allows for the coupling of the guide 150 to the moveable ring 120 of the base assembly 110. The mechanical components may be any suitable mating structure such as corresponding male to female components, snap fitting, bayonet mount and Velcro-style fasteners, or the like. One specific example of the mechanical interface is shown in FIGS. 3A and 3B. FIG. 3B shows the first mechanical component 182a and FIG. 3A shows the second mechanical component 182b. In this example, the first mechanical component 182a is a keyway, and the second mechanical component 182b is a key. FIG. 3A shows two second mechanical components 182b (i.e., two keys). While only one keyway (182a) is shown in FIG. 3B, a second keyway on the symmetrically opposite end of the arc member 154 would also be present to mate with the opposing key shown in FIG. 3A. The second mechanical component 182b (e.g., keys) may be configured to be aligned to a plane position of the guide surface 172. Also, as seen in FIG. 3B, the first mechanical component 182a (e.g., keyways) may include part of the guide surface 172. Accordingly, when mating the second mechanical component 182b (e.g., keys) with the first mechanical component 182a (e.g., keyways), the arc member 154 will have a predetermined orientation/alignment relative to the base assembly 110.

Once the guide 150 is mated with base assembly 110 via the moveable ring 120, the guide 150 is able to freely rotate via the moveable ring 120. That is, the moveable ring 120 being rotatable about the axis Ax relative to the stationary base ring 112 (as described above), and the guide 150 being coupled with the moveable ring 120, allows the guide 150 and the moveable ring 120 to rotate together about the axis Ax when a rotational force is applied to either the moveable ring 120 or the guide 150.

Figure 7:
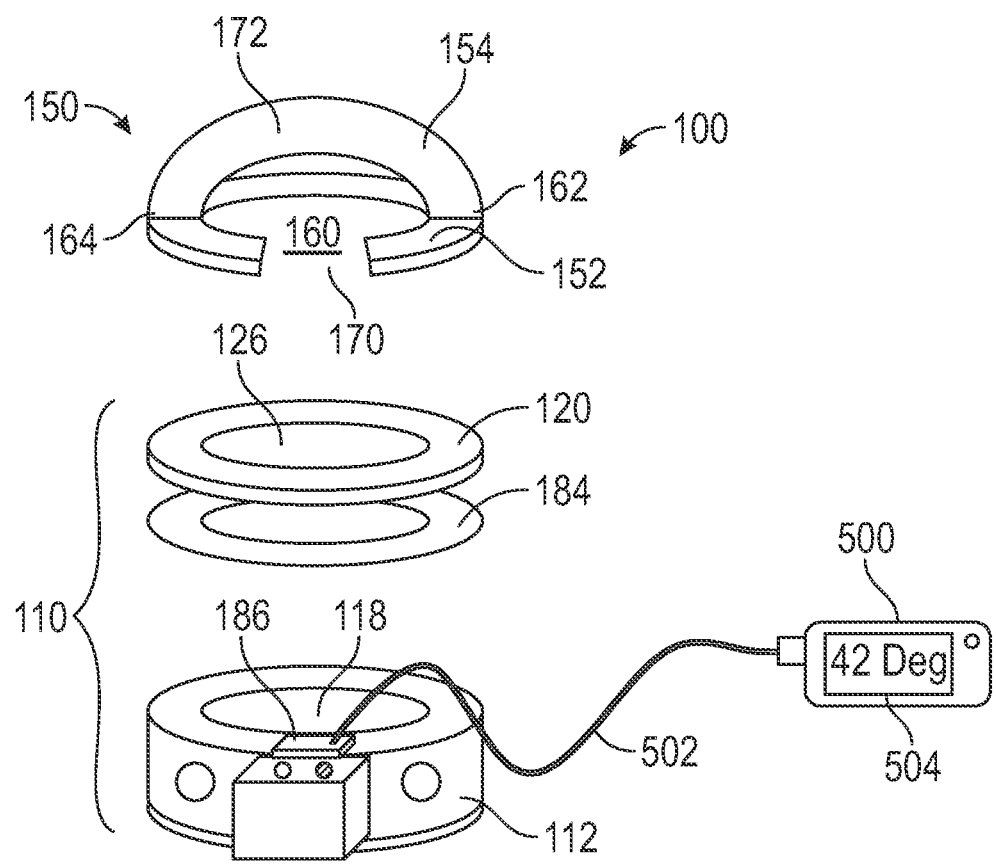
FIG. 7 is a schematic exploded perspective view of a base assembly 110 and a guide 150 of the medical guidance apparatus 100 illustrated in FIG. 1.

FIG. 7 illustrates an exploded schematic perspective view of the medical guidance apparatus 100 with additional features allowing for computer assisted positioning of the guide 150 relative to the base assembly 110. As shown in FIG. 7, the medical guidance apparatus 100 may further include a rotary encoder formed of a scale 184 and a module 186. The rotary encoder may be any known device in the art that converts angular position to an analog or digital signal. The rotary encoder may comprise the rotary scale 184 and the module 186 having a sensor head/sensor circuit board and related electronics. The rotary scale 184 may be coupled with and/or integral with moveable ring 120 such that the rotary scale 184 can rotate with the rotatable ring 120. The sensor head faces the rotary scale 184, which is mounted on the rotatable ring 120, and is electrically connected to the sensor circuit board. The rotary encoder measures an angular position of the rotatable ring 120 against the base ring 112.

A controller box 500 may be electrically connected to the medical guidance apparatus 100 via an electric cable 502. The controller box 500 may include an indicator 504, a microcontroller (not shown) and a power source (e.g., a battery) (not shown). The microcontroller may communicate with the sensor circuit board of the medical guidance apparatus 100. The sensor circuit board processes measurement signals of the angular position of the rotary scale 184 by the sensor head, and outputs the angular position to the microcontroller. The power source may power the indicator 504, the sensor circuit board, and the microcontroller. The indicator 504 may include an LED or LCD display to provide a number corresponding with the real-time rotational position of the moveable ring 120 as determined via the rotary encoder. The use of the rotary encoder to determine precise position of the moveable ring 120, and therefore the precise position of the guide 150 coupled with the moveable ring 120, allows for precise positioning of the guide 150 about the A axis. In some embodiments, the use of a controller box 500 to house one or more power sources and the microcontroller away from the medical guidance apparatus is advantageous in that it keeps any field generated by the power source away from the patient. In such embodiments, any circuit not needed to be placed within the base assembly 110 may be located within the controller box as well.

In another aspect, the moveable ring 120 may be completely absent from the needle positing apparatus 100. In such an arrangement, the bearing 128 would also be absent. In order to achieve rotational movement of the guide 150 relative to the base ring 112, in this configuration, the guide 150 may be rotationally mated with the base ring 112 via the above-described tapered sections, but without any mechanical mating components (i.e., without keys and keyways). Because the taper of the guide 150 would be geometrically congruent with the taper of the base ring 112, the guide 150 may rest concentrically on the base ring 112 such that the underside surface of the guide 150 is contacting the topside surface of the base ring 112. Friction/gravity will allow the guide 150 to stay in place on the base ring 112. The rotation of the guide 150 is still possible because the guide 150 is not mechanically connected to the base ring 112, while the base ring 112 is fixed in place. Thus, the guide 150 may be rotated about the axis Ax by manually applying rotational force on the guide 150. In other words, the guide 150 may be rotated as an inner concentric ring flush against an outer concentric ring. To that end, it may be desirable to use certain type of lubrication between frame ring 152 and base ring 112.

Figure 8:
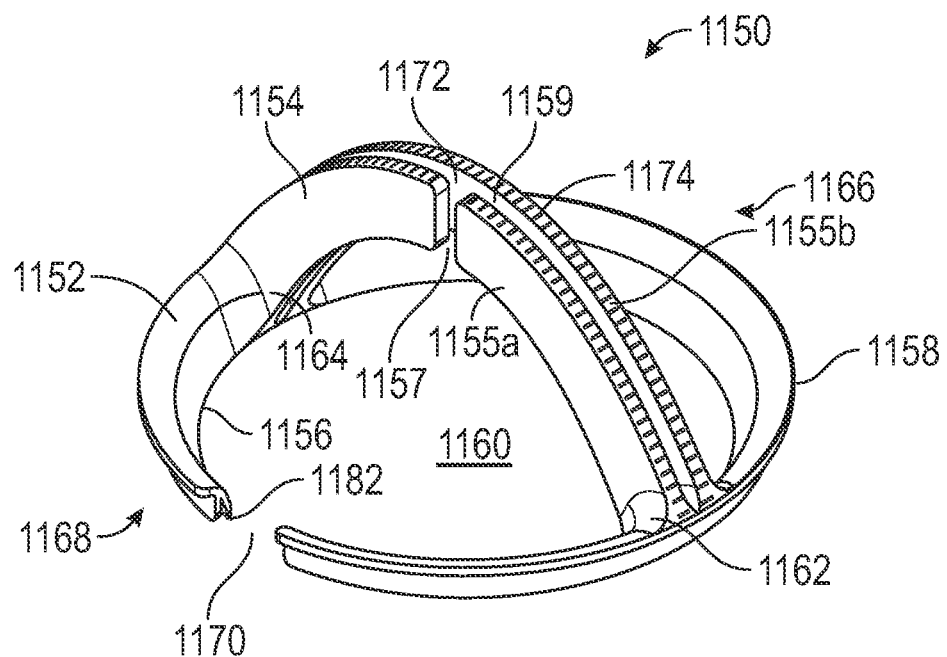
FIG. 8 is a perspective view of an example guide in accordance with certain aspects of the disclosure.

FIG. 8 illustrates a perspective view of a guide 1150 for a medical guidance apparatus, according to another embodiment. The guide 1150 is similar to the guide 150 shown in FIGS. 1-3 and similar reference numerals represent corresponding features. Thus, the guide 1150 similarly includes a frame ring 1152, an arc member 1154, an inner circumference 1156, an outer circumference 1158, an opening 1160, a first end 1162, a second end 1164, a first half 1166, a second half 1168, a gap 1170, a guide surface 1172, a plurality of angular reference marks 1174, and an arc member thickness.

The width of the ring shape of the frame ring 1152 (i.e., the distance from the inner circumference 1156 to the outer circumference 1158 in a radial direction, which is also the difference between the inner radius and the outer radius of the frame ring 1152), may be the same as in frame ring 152. The arc member 1154 may have an arc shape that spans the same angle range as in the arc member 154. The arc member 1154 may be integrally formed with the frame ring 1152 such that the entire guide 1150 is monolithically formed, as with the guide 150. Thus, the guide 1150 has the same structural and assembly advantages noted above with respect to the guide 150.

Similar to the guide 150, the guide 1150 may be coupled with a base assembly in a similar manner as described with respect to FIGS. 3A, 3B and 4. The guide 1150 may be coupled via the same mechanical components noted above or with another mechanism such as a slot 1182 shown in FIG. 8. A corresponding feature may be present on the moveable ring or base ring to couple the guide 1150 to the base assembly. The guide 1150 may rotate in the same manner as the guide 150.

The difference between the guide 1150 and the guide 150 is provided in the arc member 1154. As shown in FIG. 8, the arc member of 1154 may comprise a first arc component 1155*a* and a second arc component 1155*b*. The first and second arc components 1155*a* and 1155*b* have an arc shape and both extend from the first end 1162 to the second end 1164 of the frame ring 1152. Each of the first and second arc components 1155*a* and 1155*b* may span the same angle range from the first end to the second end. Each of the of the first and second arc components 1155*a* and 1155*b* may include angular reference marks 1174 formed on a top surface or a side surface. Each angular reference mark 1174 on the first arc component 1155*a* corresponds with another angular reference mark on the second arc component 1155*b*. Having dual reference angular reference marks 1174 allows for easer visual alignment of the instrument. The first arc component 1155*a* further includes a gap 1157 having sufficient size for the instrument to pass through the gap 1157. Additionally, the first arc component 1155*a* is separated from the second arc component 1155*b* by a space or gap 1559, which is also of sufficient size for the instrument to pass therethrough. Thus, an instrument to be guided can pass first through the gap 1157 of the first arc component 1155*a* to enter the gap 1159 between the first and second arc components 1155*a* and 1155*b*. Once the instrument is located within the gap 1159 between the first and second arc components 1155*a* and 1155*b*, the instrument can be moved along the surface 1172 between the first and second arc components 1155*a* and 1155*b*. By signifying the guidance surface 1172 with two separated physical surfaces of the first and second arc components 155*a*, 155*b*, the medical instrument does not need to touch the parts. Therefore, the operator can insert the medial instrument with superior tactile feedback. Also, with space in between the first and second arc components 1155*a*, 1155*b*, the operator can easily adjust the medical instrument to be on the guide surface 1172.

Figure 9:
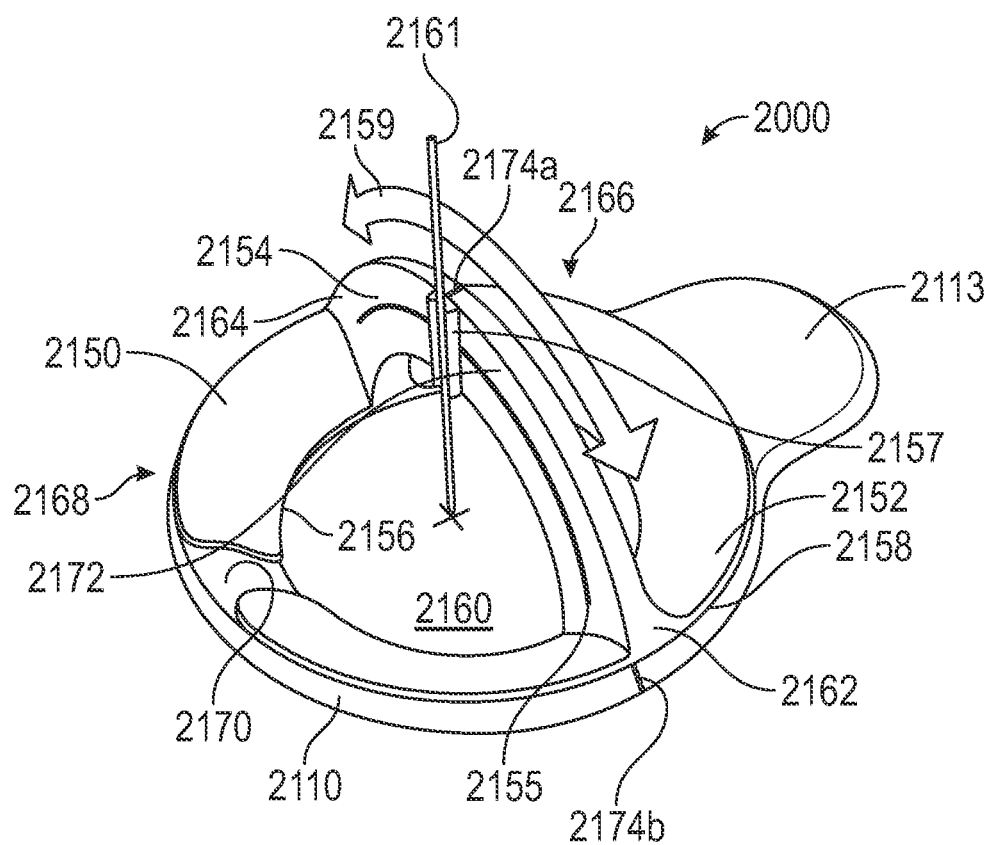
FIG. 9 is a perspective view of another example medical guidance apparatus in accordance with further aspects of the disclosure.

FIG. 9 illustrates a perspective view of a medical guidance apparatus 2000 according to another embodiment. The medical guidance apparatus 2000 includes a guide 2150 and a base assembly 2110. The base assembly 2110 and the guide 2150 are similar to the base assembly 110 and guide 150 shown in FIGS. 1-6 and similar reference numerals represent corresponding features and functions. Thus, the base assembly 2110 may similarly include a stationary base ring and a moveable ring. The guide 2150 similarly may include a frame ring 2152, an arc member 2154, an inner circumference 1156, an outer circumference 2158, an opening 2160, a first end 2162 and a second end 2164, a first half 2166, a second half 2168, a gap 2170, a guide side surface 2172, and an arc member thickness which is tapered at the first and second ends.

The width of the ring shape of the frame ring 2152 (i.e., the distance from the inner circumference 2156 to the outer circumference 2158 in a radial direction, which is also the difference between the inner radius and the outer radius of the frame ring 2152), may be the same as in frame ring 152. The arc member 2154 may have an arc shape that spans the same angle range 170 as in the arc member 154 (refer to FIG. 4). The arc member 2154 may be integrally formed with the frame ring 2152 such that the entire guide 2150 is monolithically formed, as with the guide 150. Thus, the guide 2150 has the same structural advantage as noted above with the guide 150.

Similar to the guide 150, the guide 2150 may be rotatably coupled with the base assembly 2110. The guide 2150 may be coupled via the same mechanical components noted above or with another mechanism. A corresponding feature may be present on the moveable ring or base ring to couple the guide 2150 to the base assembly 2110. The guide 2150 may rotate with respect to the base assembly 2110, in the same manner as the guide 150.

A difference between the guide 2150 and the guide 150 is provided in the arc member 2154. As shown in FIG. 9, the arc member of 2154 may comprise a rail 2155 and an instrument holder 2157. The rail 2155 may be formed in the guide surface 2172 and has an arc shape along the same arc path defined by the arc member 2154. The instrument holder 2157 may be slideable along the rail 2155 along the path shown by the arrow 2159. The instrument holder 2157 may be in the shape of a half cylindrical groove sized to receive a needle-like instrument 2161, for example a biopsy needle or ablation probe. The instrument holder 2157 may be shaped to fit other instruments, depending on the procedure desired to be conducted. The instrument holder 2157 provides constrained guidance for the instrument 2161. The instrument holder 2157 can accurately guide the instrument 2161 by directing the half cylindrical groove to an angle (trajectory) intersecting the target incision point. Thus, the instrument holder 2157 can increase accuracy and can reduce intervention time.

The instrument holder 2157 may be shaped to fit multiple instruments in a pre-set geometric configuration, for example multiple cryoablation needles arranged so that two or more needles will be held by the instrument holder 2157. For example, two needles may be held simultaneously, both positioned near the arc member 2154 or tangential to the arc member. In other examples, three, four, or more needles may be held simultaneously by the instrument holder 2157 in a triangle, square, diamond, etc. configuration. The instrument holder 2157 may provide constrained guidance for the instruments to maintain the geometric relationship between instruments (e.g., parallel insertion) during the procedure.

Another difference shown in FIG. 9 (with respect to FIG. 1) is the use of a first illumination indicator 2174*a* and a second illumination indicator 2174*b* in addition to, or in place of, physical angular reference marks 174 used in the other exemplary embodiments. That is, as seen in FIG. 9, in the arc member 2154, there are no line marks as those linear angular reference marks 174 or 1174 described in the above embodiments. Rather, as shown in FIG. 9, the illumination indicator 2174*a* may be placed along the top surface of the arc member 2154. The illumination indicator 2174*a* may serve the same function of the line markers discussed above. While one illumination indicator 2174*a* is shown on the arc member 2154 (because only one is lit up), there may be a plurality of illumination indicators along the entire span of the arc member 2154 at the same intervals of the hatch marks shown in the other example embodiments. Only one illumination indicator could be lit up during use to show the operator the exact posture (location, position, and/or orientation) where the instrument should be placed along the arc member. Thus, the illumination indicator 2174*a* in FIG. 9 is showing the current desired position of the instrument. With the illumination indictor, rather than the operator needing to visually find a particular marker along the arc, the operator can easily and quickly see where to place the instrument along the arc. The second illumination indicator 2174*b* may be provided on the outer circumference of the base assembly 2110. The illumination indicator 2174*b* may serve the same function as the first illumination indicator 2174*a* with regard to the desired rotational position of the guide 2150. The illumination indicator 2174b may indicate the insertion plane (see FIG. 15 and below discussion). Accordingly, a plurality of illumination indicators 2174b with respect to the base ring may also be present along the entire circumference, while only a single indicator is illuminated in the example shown in FIG. 9. Thus, because the operator does need to read the angular reference marks, the duration of the intervention as well as mental stress of the operator is reduced. The illumination indicators may include an LED array for which the electronics to electrically drive the array are stored in a grip 2113. It should be understood that the illumination indicators may be applied to any of the other example embodiments disclosed herein. That is, the illumination indicator is not a mutually exclusive feature and can be used in place of, or in addition to, the hatch marks. The guide surface 2172 and/or the entire second half 2168 of the frame ring 2152 may be a different color than the side of the arc member opposite the guide surface and/or the first half 2166 of the frame ring 2152.

Another optional feature of some embodiments that is illustrated in FIG. 9 is a differentiating marker located on the guide 2150. The differentiating marker is shown as a different color or hue located on the surfaces of the guide 2150 visible during use. This color differentiates the portion of the medical guidance apparatus where the needle will be placed and guided. The differentiating marker may be, for example, a different color, an adhesive material, a pattern, or some other differentiator that the physician can use to quickly differentiate which portion of the device should be used during needle placement.

Figure 10:
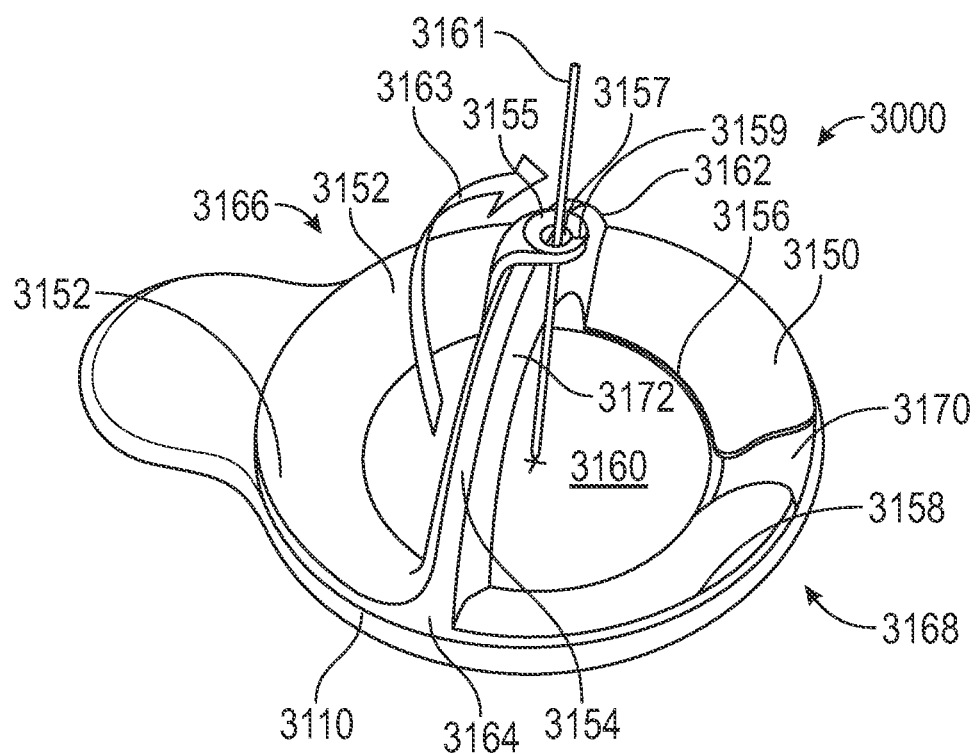
FIG. 10 is a perspective view of another example medical guidance apparatus in accordance with aspects of the disclosure.

FIG. 10 illustrates a perspective view of a medical guidance apparatus 3000 according to a further embodiment. The medical guidance apparatus 3000 includes a guide 3150 and a base assembly 3110. The base assembly 3110 and the guide 3150 are similar to the base assembly 110 and guide 150 shown in FIGS. 1-6 and similar reference numerals represent corresponding functions and features. Thus, the base assembly 3110 may include a stationary base ring and a moveable ring similar to those shown in FIG. 3A. The guide 3150 may similarly include a frame ring 3152, an arc member 3154, an inner circumference 3156, an outer circumference 3158, an opening 3160, a first end 3162, a second end 3164, a first half 3166, a second half 3168, a gap 3170, a guide surface 3172, and an arc member thickness.

The width of the ring shape of the frame ring 3152 (i.e., the distance from the inner circumference 3156 to the outer circumference 3158 in a radial direction, which is also the difference between the inner radius and the outer radius of the frame ring 3152), may be the same as in frame ring 152. The arc member 3154 may have an arc shape that spans the same angle range as in the arc member 154. The arc member 3154 may be integrally formed with the frame ring 3152 such that the entire guide 3150 is monolithically formed, as with the guide 150. Thus, the guide 3150 has the same structural advantage as noted above with the guide 150.

Similar to the guide 150, the guide 3150 may be rotatably coupled with the base assembly 3110. The guide 3150 may be coupled via the same mechanical components noted above or with another mechanism. A corresponding feature may be present on the moveable ring or base ring to couple the guide 3150 to the base assembly 3110. The guide 3150 may rotate relative to its base assembly in the same manner as the guide 150.

As shown in FIG. 10, a difference between the guide 3150 and the guide 150 is that the guide 3150 comprises an instrument holder 3155. The instrument holder 3155 includes a through-hole 3157. The through-hole 3157 may be large enough to loosely hold an instrument 3161. The instrument holder 3155 may further include a slit 3159. The slit 3159 provides a passageway for the instrument 3161 to reach the through-hole 3157 after the instrument has been inserted. The instrument holder 3155 may be made from a material having sufficient flexibility/deformability to allow the slit 3159 to expand when applying force to move the instrument 3161 through the slit 3159. The material should also have sufficient resistance to flexibility/deformability that the slit 3159 returns to the original configuration shown in FIG. 10 when force by the operator is no longer being applied. In this manner, once the instrument 3161 is located in the through-hole 3157, the instrument 3161 will not unintentionally exit the slit 3159.

While not visible in FIG. 10, the side of the arc member 3154 opposite the guide surface 3172 may comprise a rail similar to the rail shown FIG. 9. The rail may have an arc shape along the same arc path defined by the arc member 3154. The instrument holder 3155 may be slideable along the rail along in the same direction shown by arrow 2159 in FIG. 9. The instrument holder 3155 may also be retractable from the arc member 3154 along the arrow 3163 and attachable to the side of the arc member opposite the guide surface 3172. The instrument holder 3155 may be shaped to fit other instruments, depending on the procedure being conducted.

The instrument holder 3155 provides constrained guidance for the instrument 3161. The instrument holder 3155 can accurately guide the instrument 3161 by directing the instrument 3161 to the target trajectory. With the instrument holder 3155, the instrument 3161 can move freely within the through-hole 3157 without the instrument 3161 falling down even when the operator is no longer holding the instrument 3161. Therefore, the instrument holder 3155 can improve handling management of the instrument 3161 throughout the procedure.

Figure 11:
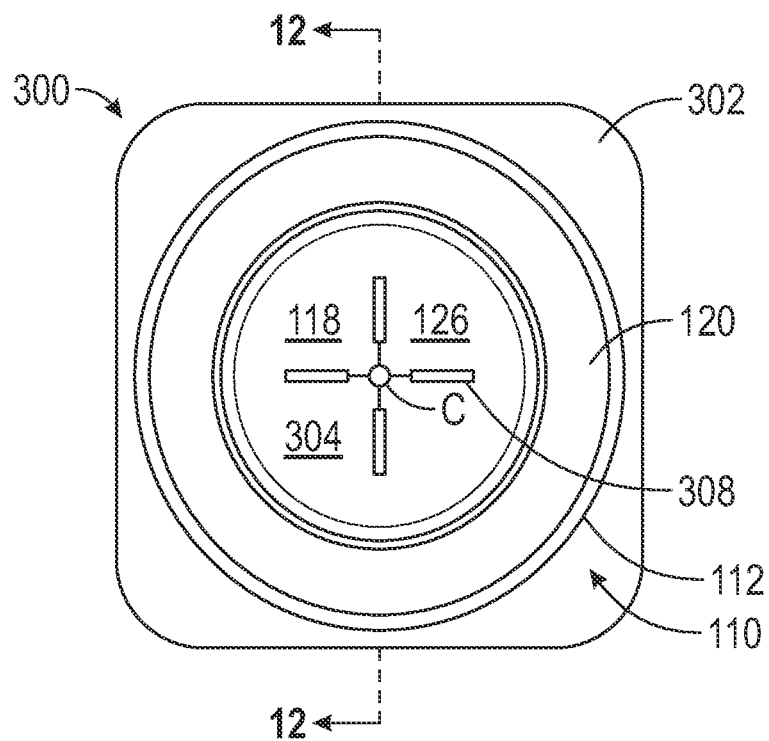
FIG. 11 is a top view of the base assembly 110, without the guide 150 and with an adhesive marker 300, of the medical guidance apparatus 100 illustrated in FIG. 1

FIG. 11 illustrates a top view of the base assembly 110, with the guide 150 removed. The same base assembly 110 can be applied to the guide 3510. FIG. 11 illustrates an example embodiment of the base assembly 110, where an adhesive marker 300 has been attached to an underside surface of the base assembly 110. The adhesive marker 300 may include a backing material 302, a peel-away portion 304 aligned with the openings 118 and 126, and an adhesive 306. The adhesive 306 may be any known adhesive suitable for use on human skin while having sufficient strength to maintain the position of the medical guidance apparatus on the patient during the procedure. Examples of adhesives are surgical tapes and medical tapes that hold onto the skin but can be removed without damaging the skin. The adhesive marker 300 may be directly attached to the underside surface of the base ring 112. The attachment may be achieved with another layer of adhesive (not shown) on the upper surface 303 of the backing material or any other known attaching mechanism. The adhesive marker 300 may include a center marker 308 located on the peel-away portion 304. As shown in FIG. 11, the center marker 308 may comprise a plurality of lines whose intersection defines a single point, e.g., a cross pattern. The center marker 308 allows the operator to easily align the center point C with the desired entry point on the patient. Other than the center marker 308, the backing material 302 may be transparent.

In some embodiments (not shown), there is also included one or more tabs on the base assembly 110. These tabs are useful, for example, for including additional area for adhesion, where the tabs may have the same adhesive 306 discussed above or an additional adhesive. Alternatively, or in addition, the tabs do not have an adhesive but provide additional support when patient mounted and/or provide a surface for the use of surgical tape or another fixation component to be used to secure the base assembly 110 to the patient. The use of these one or more tabs works in concert with the high rigidity of the monolithic structure. The tabs can be rigidly mounted or may be hinged to allow the device to conform to different anatomies.

Figure 12:
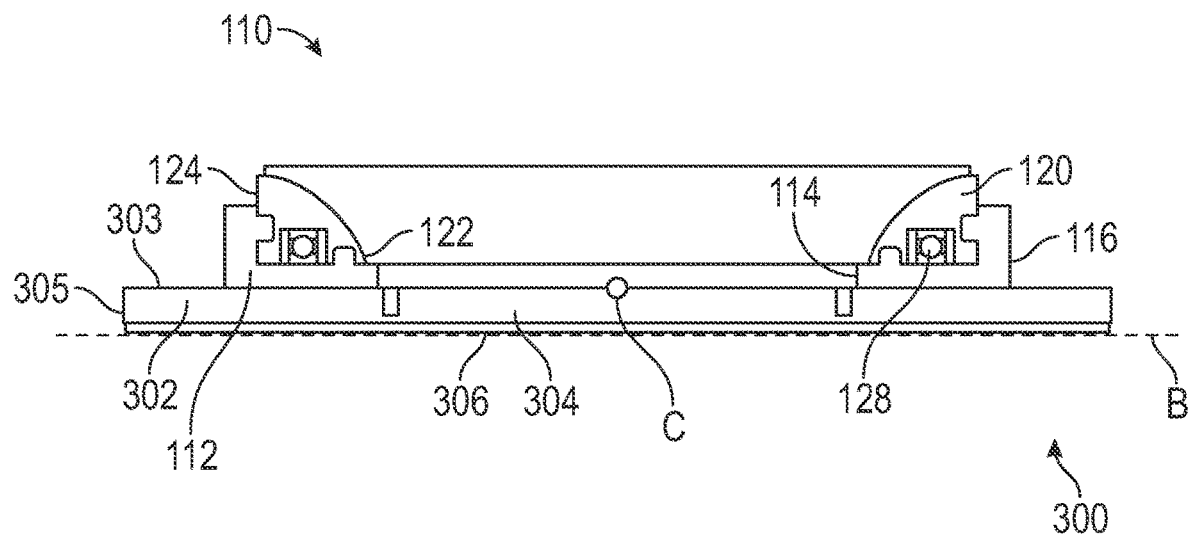
FIG. 12 is a cross sectional view taken along line 12-12 of the base assembly 110 illustrated in FIG. 11, prior to removing a peel-away portion of the adhesive marker.
Figure 13:
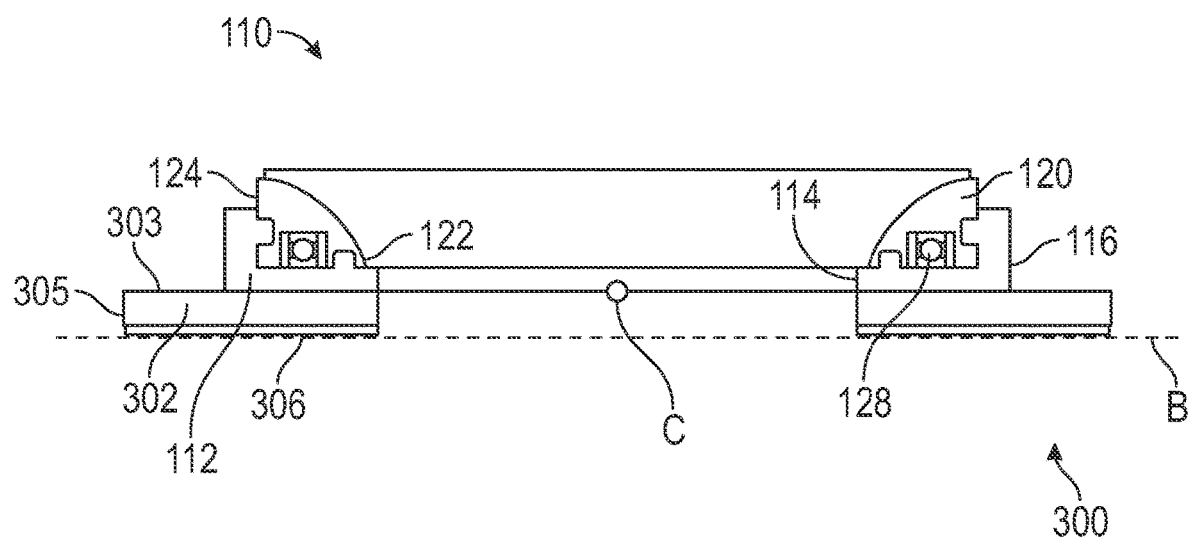
FIG. 13 is a cross sectional view taken along line 12-12 of the base assembly 110 illustrated in FIG. 11, after removing a peel-away portion of the adhesive marker.

FIG. 12 is a cross sectional view taken along line 12-12 of FIG. 11 prior to the removal of the peel-away part 304. FIG. 13 is a cross-sectional view taken along line 12-12 of FIG. 11 after the peel-away portion 304 has been removed. As shown in FIG. 12, the base assembly 110, and more particularly the base ring 112, has the adhesive marker 300 attached to the underside surface of the base assembly. The adhesive 306 extends across the entire underside surface 305 of the adhesive backing material 302, including the peel-away portion 304. In the state shown in FIG. 12, the backing material 302, including the peel-away portion 304, with the adhesive 306, is in contact with the surface B (i.e., the patient's skin), thus fixing the base assembly 110 to the patient. After the operator has aligned the center marker 308 such that the center point C is aligned with the insertion point on the surface B, the operator may peel away the peel-away portion 304, thus exposing the openings 118, 126 to the surface B. The backing material may include a perforation portion (not shown) defining the peel-away portion 304 to allow the operator to peel away the peel-away portion 304. The back material may also include a tab for gripping or any other mechanism to assist in the peeling away the peel-away portion 304. This is the state is shown in FIG. 13, where there is no longer any backing material in the openings of the base ring 112 and the moveable ring 120. The dimensions of the backing material 302 and the adhesive 304 are exaggerated for clarity and it should be understood that the relative dimensions of the base ring 112 and moveable ring 120 are not to scale with the dimension of the backing material 302 and the adhesive 304. That is, in the practice, the thickness (or vertical height in FIGS. 12 and 13) of the backing material 302 and adhesive 304 is several orders of magnitude smaller than the height of the base ring 112 and moveable ring 120 (e.g., micron scale vs centimeter scale). Thus, in practice, the underside of the base ring 112 would essentially be nearly touching the surface B, even with the adhesive marker 300.

It should be understood that the above-described adhesive marker 300 is not a mutually exclusive feature and can be applied to any of the example embodiments described herein. That is, the adhesive marker 300 can be applied to the underside surface of any of the medical guidance apparatuses described herein in order to affix and properly align the base assembly to the operation spot on the patient.

Figure 14:
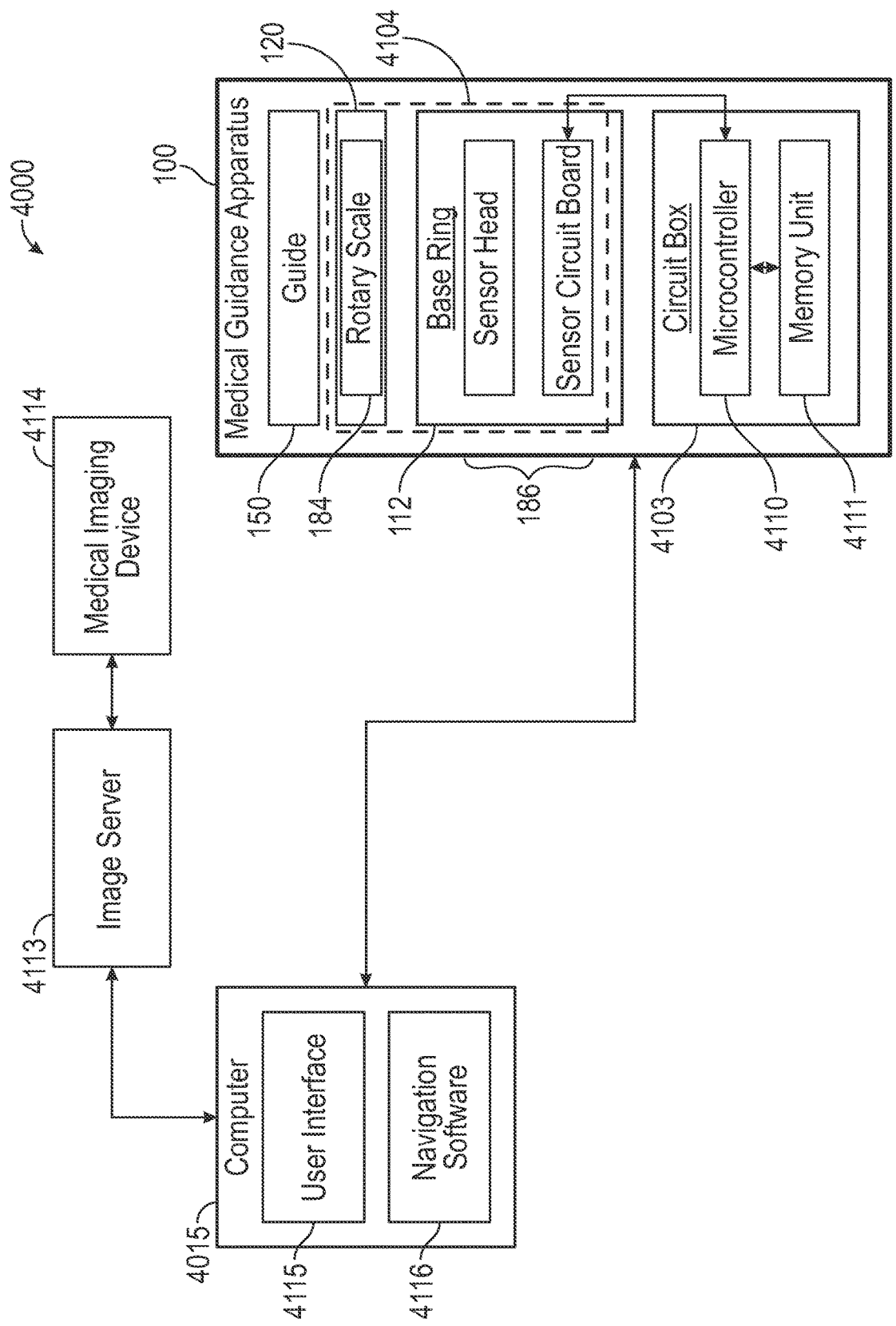
FIG. 14 is a functional block diagram illustrating an example medical guidance system in accordance with aspects of the disclosure.

Turning to the method of using the medical guidance apparatuses 100, 1000, 2000, 3000 described above, FIG. 14 is a functional block diagram illustrating a medical guidance system 4000 according to another embodiment of the present disclosure. For simplicity, reference numbers from the embodiment of the medical guidance apparatus 100 are used hereinafter. However, it should be understood that the following discussion is applicable to all of the embodiments discussed in the present disclosure. The medical guidance system 4000 transmits and receives data to/from an image server 4113 that receives image data from a medical imaging device 4114. The medical guidance system 4000 includes a computer 4015 and a medical guidance apparatus 100 that are communicatively-coupled via a bus. The image server 4113 includes, but is not limited to, a PACS (Picture Archiving and Communication System) server or equivalent that receives image data from the medical imaging device 4114 and stores the image data in DICOM® format. The medical imaging device 114 includes, but is not limited to, a computed tomography (CT) scanner, magnetic resonance imaging (MRI) scanner, positron emission tomography (PET) scanner, single-photon emission computed tomography (SPECT) scanner, a fluoroscopy scanner, or combinations thereof.

The computer 4015 of the medical guidance system 4000 includes, among other things, a user interface 4115 and navigation software 4116. The user interface 4115 allows a user to access and control the computer 4015 to determine, according to navigation software 4116, proper insertion angles of a needle-like medical device into a medical patient based on image data received from the medical imaging device 4114 and stored in the image server 4113. Additionally, the navigation software 4116 provides the operator information including, but not limited to, protocols involving the use of the medical guidance apparatus 100 and visual orientation and location information of the medical guidance apparatus 100.

The medical guidance apparatus 100 includes or is operatively connected to a guide 150 coupled to the base movable ring 120 of the base assembly 110. As shown in FIG. 7, the base movable ring 120 includes the rotary scale 184 and module 186. A microcontroller 4110, a memory unit 4111, and a circuit box 4103 are equivalent to the control box 500 also shown in FIG. 7.

The base ring 112 may include fiducial markers (not shown) at four corners around the base ring or on/within the grip 113. The fiducial markers are visible optically as well as in CT and X-ray images utilizing radio-opaque material. The radio-opaque material can be, but is not limited to, plastic including fillers of Barium Sulfate, bismuth subcarbonate, bismuth oxychloride, tungsten. At each corner, the fiducial markers form a cluster of markers with different numbers of fiducial markers at each corner. Therefore, the position and the orientation of the base ring 112 can be geometrically distinguished using only the fiducial markers in the CT and X-ray images.

As noted above the axis Ax passes through a point C on the mounting surface B and the angular reference marks 174 are line marks to signify an angle around point C on the guide surface 172 (refer to FIG. 4) of arc member 154. By rotating the moveable ring 120 together with the guide 150 around axis Ax, the angular reference marks 174 also rotate around axis Ax. By using the angular reference marks 174, the medical apparatus guide 100 localizes the insertion plane and further localizes fine grids of a remote center of motion with point C. The grids are cone-shaped grids with generator E along the point C as a pivot.

The remote center of motion models an operator's maneuver of a needle-like medical tool. Thus, point C is aligned to a skin entry point of the medical tool, which is defined by considering obstacles close to the patient's skin. With the fixed point C, the operator can select an intended trajectory to the target by using an appropriate relation between the rotatable ring 120/guide 150 and the angular reference marks 174.

After determining the position of rotatable ring 120 (thereby also the guide 150) and the angular reference marks 174, the operator can insert the needle-like medical tool with guidance from guide 150 at the target angular reference marks 174.

The microcontroller 4110 processes information from the computer 4015 and the sensor circuit board 4107 and the microcontroller 4110 communicates with the computer 4015 and the sensor circuit board 4107 to exchange commands and target information between them. Specifically, the microcontroller 4110 initiates and sends the angular position of the moveable ring 120 measured by the rotary encoder to the computer 4015, as needed.

The microcontroller 4110 is also electrically-connected to the memory unit 4111. The memory unit 4111 stores at least transformation matrices of the medical guidance apparatus 100 based on a local coordinate of the medical guidance apparatus 100, which is determined as design. The microcontroller 4110 then retrieves and sends these transformation matrices in the memory unit 4111 to the computer 4015, when the navigation software 4116 requires them.

Specifically, the circuit box 4103 is electrically-connected to the rotary encoder 4104 at the sensor circuit board 4107 in base ring 112 via the electric cable, as a separate part from the base ring 112. Consequently, the circuit box 4103 in can be placed bedside or near the patient close to an area of the intervention, but in a separated place from base ring 112. With the circuit box 4103 being separate from base ring 112, the base ring 112 can reduce the footprint and reduce the area needed for the intervention. Also, the circuit box 4103 includes an indicator. The indicator reflects the real-time angular position of the moveable ring 120 with a digital indicator. Moreover, the indicator displays different information about the medical guidance apparatus 100, for instance the target angular position of the moveable ring 120, the target angular reference mark, comparison between the target and current angular position of the moveable ring 120, and an estimated amount of the remaining battery power. With the indicator on the circuit box 4103, the operator can confirm the information on the medical guidance apparatus 100 on the spot without having to leave the patient and the area of the intervention.

Figure 15:
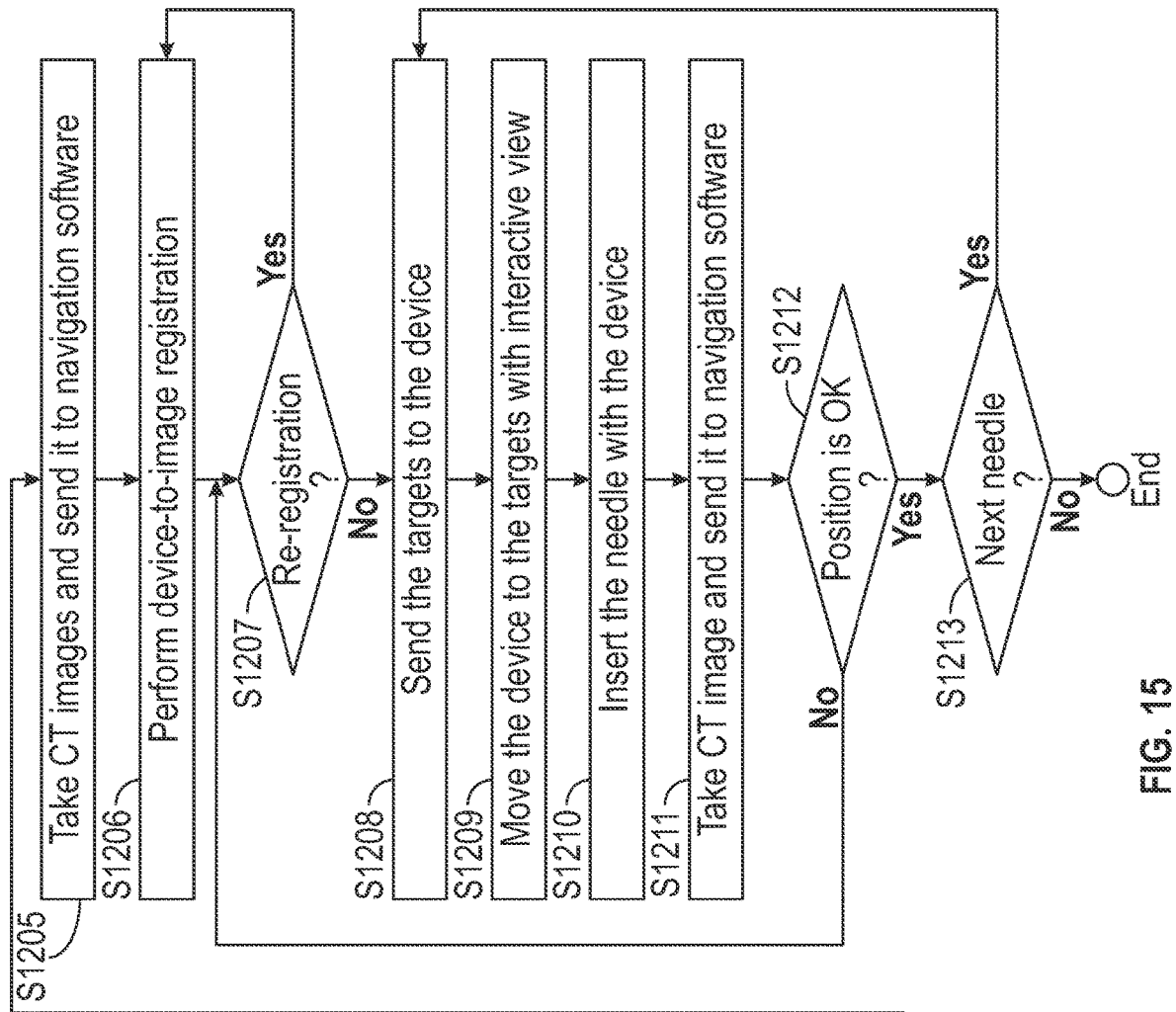
FIG. 15 is a flowchart illustrating a process for guidance of a needle-like instrument using a medical guidance system in accordance with aspects of the disclosure.

FIG. 15 is a flowchart illustrating an exemplary process for guidance of a needle-like instrument using the medical guidance apparatus 100 under control of system 4000. In step S1201 an operator takes medical images using the medical imaging device 4114. The medical imaging device 4114 is a CT scanner in this particular embodiment, and sends the CT images to the navigation software 4116 in the computer 4015 via the image server 4113.

At step S1202, with the CT images being displayed by the user interface 4115, the operator defines one or more targets for percutaneous intervention with a needle-like medical tool and the skin entry point. At the same time, by virtually connecting the target to the skin entry point, the operator can determine the plane for the trajectory of insertion of the needle-like medical tool using the navigation software 4116. Also, in this step, the operator marks the skin entry point on the patient which is standard practice using for example, grid visible markers (as those shown in FIG. 11) on the patient.

In step S1203 the operator sets up the device to calibrate it and sets a proper initial state of the medical guidance apparatus 100. More specifically, step S1203 includes setting up the rotary encoder 4104 to establish an original zero position properly.

After setting up the device, in Step S1204 the operator mounts the medical guidance apparatus 100 onto the patient aligning the point C to the skin entry point. When the adhesive marker 300 is being utilized, the operator may align the center marker 308 to the skin entry point (incision point), and then attach the medical guidance apparatus 100 in place via the adhesive 306. The operator then may remove the peel-away portion 304 of the marker 300 to expose the patient's skin.

In Step S1205, after the device mounting, the operator takes CT images including the medical guidance apparatus 100 and sends the CT images to the navigation software 4116. Using the CT images with the medical guidance apparatus 100 showing, in Step S1206 the operator conducts device-to-image registration. In this step, the navigation software 4116 recognizes the position and orientation of the medical guidance apparatus 100 on the patient in the CT images, i.e. in the coordinate of the CT image, by using fiducial markers located on the corners of the base ring 112. This fiducial marker detection can be manually performed by operator instruction via the user interface 4115 or, can be fully automated by using a computer algorithm. The detected fiducial markers are compared with the designed geometrical configuration of the fiducial markers in the medical guidance apparatus 100, then the navigation software can recognize the position and the orientation of the medical guidance apparatus 100 in CT images. The navigation software 4116 can also reflect the plan of the trajectory with two device parameters, which are angular position of the moveable ring 120 and insertion angle of guide 150 at this step.

In step S1207, the operator can be asked whether the device-to-image registration is appropriate or not by the navigation software 4116. If not (no is Step S1207), the operator can conduct Step S1206 repeatedly until the device-to-image registration is acceptable.

If the device-to-image registration is appropriate (Yes in Step S1207), the control flow proceeds to Step S1208 where the operator can send the target device parameters to the microcontroller 4110.

Afterwards in Step S1209, the operator manually rotates the guide 150 via the moveable ring 120 while the navigation software 4116 interactively updates the cross sectional image on the guide surface by using the real-time angular position of the moveable ring 120 from the microcontroller 4110. Also, the microcontroller 4110 compares the real-time angular position of the moveable ring 120 with the target angular position. Once the moveable ring 120 reaches the target angular position, the microcontroller 4110 informs the navigation software 4116 and indicator 504 of the end of targeting of the moveable ring 120. Then, the navigation software 4116 and/or indicator 504 informs the operator of the end of targeting.

Upon establishing the target angular position of the moveable ring 120 (and thereby the guide 150), in Step S1210 the operator picks the specific angular reference mark 174 indicated by the target insertion angle on guide 150 and with the specific angular reference mark 174, the operator inserts the needle-like medical tool from the skin entry point to the target. In the case of the medical guidance apparatus 100 (as shown FIGS. 1-6), the operator may slide the needle-like medical tool along the guide surface 172 until reaching the appropriate angular reference mark 174. In doing so the operator may apply force in the direction D. However, due to the structural advantages discussed above provided by the closed/monolithic structure of the guide 150, the arc member 154 is able to fully support the force without deflection or bending. In the case where the guide 1150 (FIG. 8) is being used, the operator will pass the needle-like medical tool through the gap 1157 into the area 1159 between the two arc member components 1155a and 1155b. The operator will then move the needle-like medical tool along the arc shape until arriving at the appropriate marker 1174. The guide surface 1172 also has the structural advantages noted above. In the case where the guide 2150 (FIG. 9) is being used, the operator will pass the needle-like medical tool through the instrument holder 2157. The operator will then move the needle-like medical tool along the rail 2155 via the instrument holder 2157 until arriving at the appropriate marker indicator 2174a (or marker in the case of a marker being present). The guide surface 2172 also has the structural advantages noted above. In the case where the guide 3150 (FIG. 10) is being used, the operator will advance the instrument holder 3155 (if not already advanced) along the direction arrow 3163 the instrument holder 3155 is positioned against the arc member 3154. Next, the operator will pass the needle-like medical tool through the through-hole 3157 of the instrument holder 3155. The operator will then move the needle-like medical tool along the rail via the instrument holder 3155 until arriving at the appropriate marker indicator or marker. The guide surface 3172 also has the structural advantages noted above.

In Step 1211, after the first attempt of instrument insertion, the operator takes CT images of the inserted needle-like medical tool and the medical guidance apparatus 100 using the medical imaging device 4114. The system 4000 sends the CT images to the computer 4015 to be processed by the navigation software 4116. With the CT images of the inserted needle-like medical tool, the operator evaluates the position of the inserted needle-like medical tool.

In step S1212, the position of the inserted needle-like medical tool is checked, and if the operator thinks the position is suboptimal (No in Step S1212), the flow proceeds back to Step S1208 where the operator can update the trajectory to improve the position of the needle-like medical tool with navigation software 4116. At the same time, at step S1207, with the latest CT image, the operator checks for any dislocation (movement) of one or more of the target, skin entry point, of medical guidance apparatus 100. If any dislocation is found, the operator (or system) updates the registered position and orientation of medical guidance apparatus 100. Thus, the operator can conduct device-to-image re-registration with the latest CT images. By updating the device-to-image registration, the operator can reduce discrepancy of the actual geometrical relationship between the medical guidance apparatus 100 and the target. Specifically, since the medical guidance apparatus 100 is mounted on the patient and can move with the patient body together, the update of the device-to-image registration can effectively compensate rigid dislocation of the patient from the previously obtained (older) CT images.

With an updated plane of the trajectory and the device-to-image registration, the operator can perform another attempt of the insertion with the same steps S1208-S1211 as in the first attempt.

In step S1212, if the position of the inserted needle-like medical tool is checked and the operator is satisfied with the results (Yes in Step S1212), flow continues to Step S1213. In Step S1213, a determination is made as to whether insertion of another needle-like medical tool is needed. If insertion of another needle-like medical tool is needed (Yes in Step S1213) flow returns back to Step S1208 where the coordinates of target for the next needle-like medical tool are sent to the medical guidance apparatus 100. If insertion of another needle-like medical tool is not needed (No in Step S1213) flow is complete. When inserting another needle-like medical tool, the operator may decouple the guide 150 from the base assembly 110 as necessary without needing to unmount the base assembly 110. In the case of inserting another needle-like medical tool in one of the guides 2150, 3150, the operator must remove the previous needle-like medical tool from the instrument holder 2157, 3155.

Once all of the needle-like medical tools have been inserted, the operator may decouple the guide 150 from the moveable ring 120. Once the guide 150 has been decoupled and can be freely lifted away, the operator may orient the guide 150 such that each of the needle-like medical tools pass through the gap 170. Thus, the guide 150 is completely removable from the procedure site, even when the needle-like medical tool is tethered, such as for percutaneous ablation probes.

FIGS. 16 through 20 provide various views of the subject disclosure incorporating the use of a probe holder 600, for holding a needle-like medical tool (e.g. a biopsy needle). The probe holder 600 is slideably attached to the arc member 154 and may be removable from the arc member 154 in various embodiments. The probe holder 600 is configured to slide about the arc member 154 while maintaining a constant trajectory for contacting the intended target/patient by a medical instrument. In other words, regardless of the angle at which the probe holder 600 is positioned along the arc member 154, the target puncture point for the medical instrument is constant, while the angle of entry into the target/patient is varied. It is further contemplated that, in some embodiments, the holder 600 could simultaneously hold multiple medical instruments corresponding to multiple puncture points.

Figure 20:
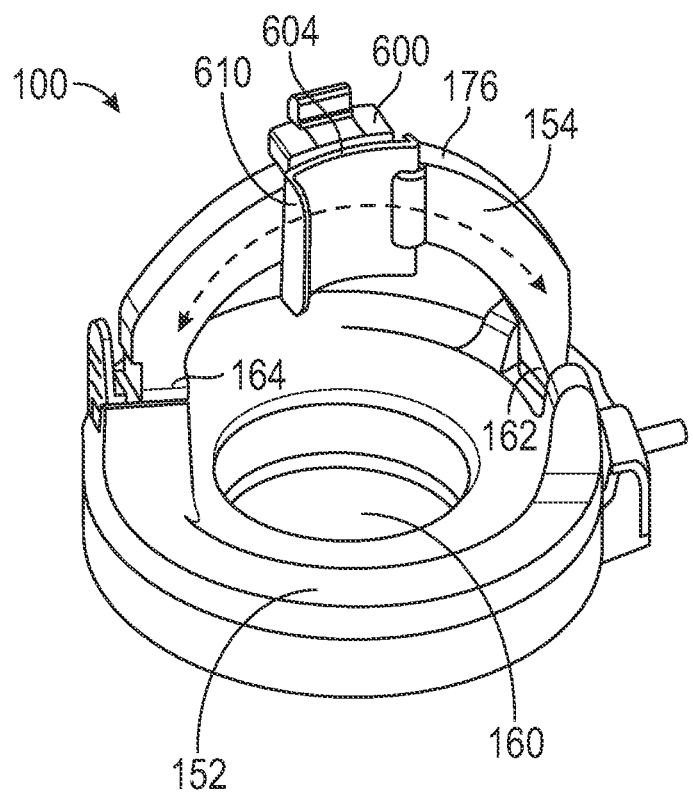
FIG. 20 illustrates a perspective view of an exemplary medical guidance apparatus 100 having a probe holder 600 mounted on the guide 150, in accordance with one more embodiment or partial embodiment of the subject disclosure.

FIG. 20 provides a perspective view of the probe holder 600 attached to the medical guidance apparatus 100, and more specifically, the probe holder 600 is attached to the arc member 154. The arrows forming the arc represent the angular movement for the holder 600 while configured upon the arc member 154. The image further depicts the frame ring 152 supporting the arc member 154, and the opening 160 providing access to a target area. The probe holder 600 includes a locking lever 604 for locking the probe in the desired position on the arc member 154, as well as a door 610.

Figure 16:
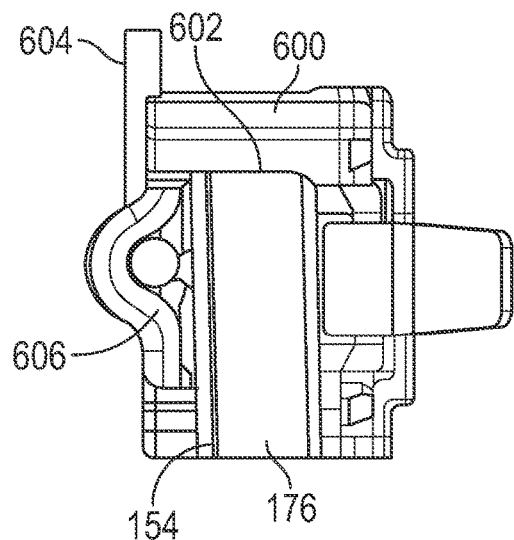
FIG. 16 provides a side perspective view of a probe holder 600 mounted on an arc member 154 to be attached to an exemplary medical guidance apparatus, in accordance with one more embodiment or partial embodiment of the subject disclosure.
Figure 17:
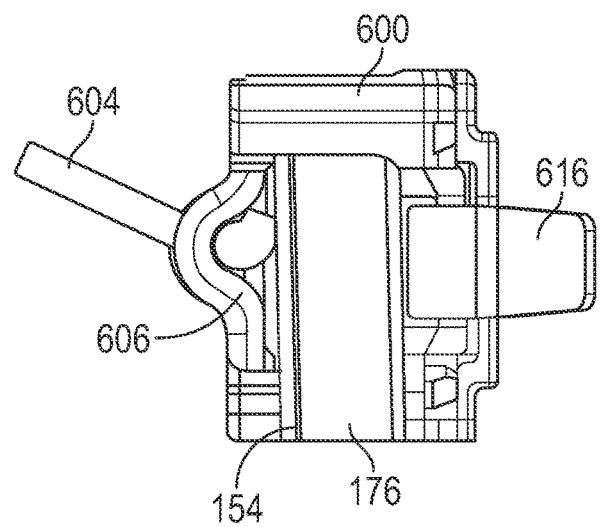
FIG. 17 provides a side perspective view of a probe holder 600 to be attached to an exemplary medical guidance apparatus, in accordance with one more embodiment or partial embodiment of the subject disclosure.

The probe holder 600 comprises an opening or fissure 602 for passage of the arc member 154, as well as a locking lever 604 configured to affix the probe holder 600 to the arc member 154 at the desired position. The locking lever 604 may be a cam lock or other releasable fastening means. Although the locking lever 604 is configured on the side of the probe holder 600 in the exemplary embodiment, it is contemplated that the locking lever 604 may be arranged in other positions upon the probe holder 600, which may be more accommodating. FIG. 16 and FIG. 17 depict an example of a locking lever 604 having a cam arm 606. FIG. 16 shows the locking lever 604 in a closed position, and FIG. 17 shows the locking lever 604 in an open position. Manipulation of the locking lever 604 allows for sliding movement of the probe holder 600 about the thickness 176 of arc member 154. The cam arm 606 of the locking lever 604 can be seen both engaged and disengaged with the arc member 154 in FIGS. 16 and 17, respectively.

Figure 18:
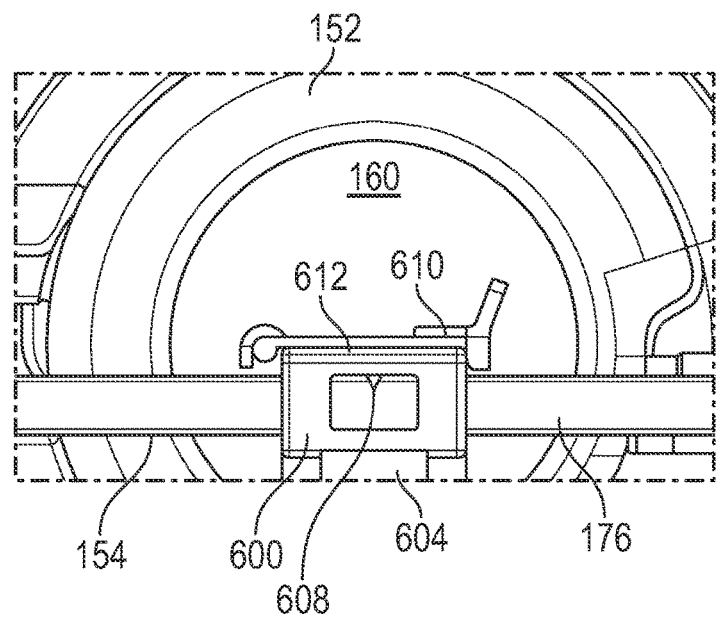
FIG. 18 provides a top view of a probe holder 600 to be attached to an exemplary medical guidance apparatus, in accordance with one more embodiment or partial embodiment of the subject disclosure.
Figure 19:
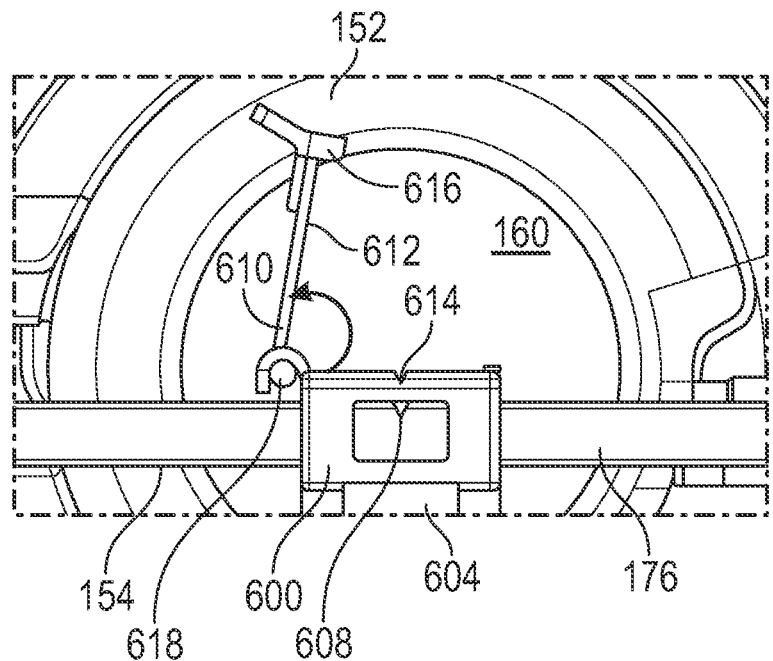
FIG. 19 provides a top view of the probe holder 600 to be attached to a medical guidance apparatus, in accordance with one more embodiment or partial embodiment of the subject disclosure.

FIGS. 18 and 19 show top views of the probe holder 600 mounted on the arc member 154 upon the guide 150. The probe holder 600 comprises an indicator 608 configured atop the probe holder 600 which is intended to correspond to the angular reference marks 174 which may be provided on the thickness 176 of the arc member 154. In other embodiments, the indicator 608 may be configured on additional or alternative locations on the probe holder 600, for added ease of viewing by the end user. In yet additional embodiments, the indicator 608 may utilize a transparent window with a convex lens (not shown) for magnifying the angular reference marks 174.

The probe holder 600 further comprises a hinged door 610 configured to accept and retain a probe. In FIG. 18, the door 610 is in the closed position, while, in FIG. 19, the door 610 is in the open position. The door 610 includes a groove or tab 612 configured to mate with a groove 614 on the probe holder 600, creating a compression fit for holding the probe (not shown). The tab 612 and/or groove 614 may be constructed of various pliable materials to accommodate various sizes (gauges) of probes to be held by the probe holder 600. In addition, the shape and length of the tab 612 and/or groove 614 may be modified to accommodate various probe sizes (gauges) and configurations. In various other embodiments, there may be multiple corresponding tabs 612 and grooves 614 to accommodate additional probes within the probe holder 600.

FIG. 19 depicts the hinged door 610 in the open position, detailing a hinge 618, the tab 612, the groove 614, and a lock 616 of the probe holder 600. Although a hinged door 610 and lock 616 are depicted, it is contemplated that alternative closure means may be utilized, including, but not limited to, a slideable closure or collapsible closure. In addition, the door 610 may be removable or replaceable, wherein replacement doors may comprise a variety of grooves to accommodate additional probe sizes (gauges) or may be configured to accommodate other medical instruments. Although the exemplary door 610 incorporates a hinge 618 and a lock 616 in the closed position, additional closure means may be incorporated, including, but not limited to, a pin, a set screw, cam lock, key, and other alternatives and derivatives. For example, door 610 may be configured to hold a needle-like instrument against the groove 614 with an adjustable holding force, as described below with reference to FIG. 28A.

In some embodiments, the probe holder 600 may be configured to be removable from the guide 150, with or without the arc member 154, as described in FIGS. 22A-27B. Some reasons for removal would be to support different gauge needles, change the location of the center of motion (i.e. move the needle slot farther radially to avoid collision with previously inserted probes), or to have multiple angle slots in a specific pattern. The probe holder 600 may be removed by having an opening where it can be lifted away from the arc. This opening may be lockable with, by example, a pin or door. In addition, the probe holder 600 can be removed by having multiple sections, held together by, for example, by screws, snaps or other fastening means. In the hinged arc member 154, the probe holder 600 may be configured to slide off the free end of the arc member 154.

FIG. 20 illustrates a perspective view of the probe holder 600 attached to the medical guidance apparatus 100, and more specifically, attached to the arc member 154. The arrows formed on the arc represent the angular movement for the holder 600 while the holder is mounted on the arc member 154. As shown in FIG. 20, the probe 600 includes the locking lever 604 for locking the probe in the desired position along the arc member 154, as well as the door 610, which is in the closed position.

Figure 21A:
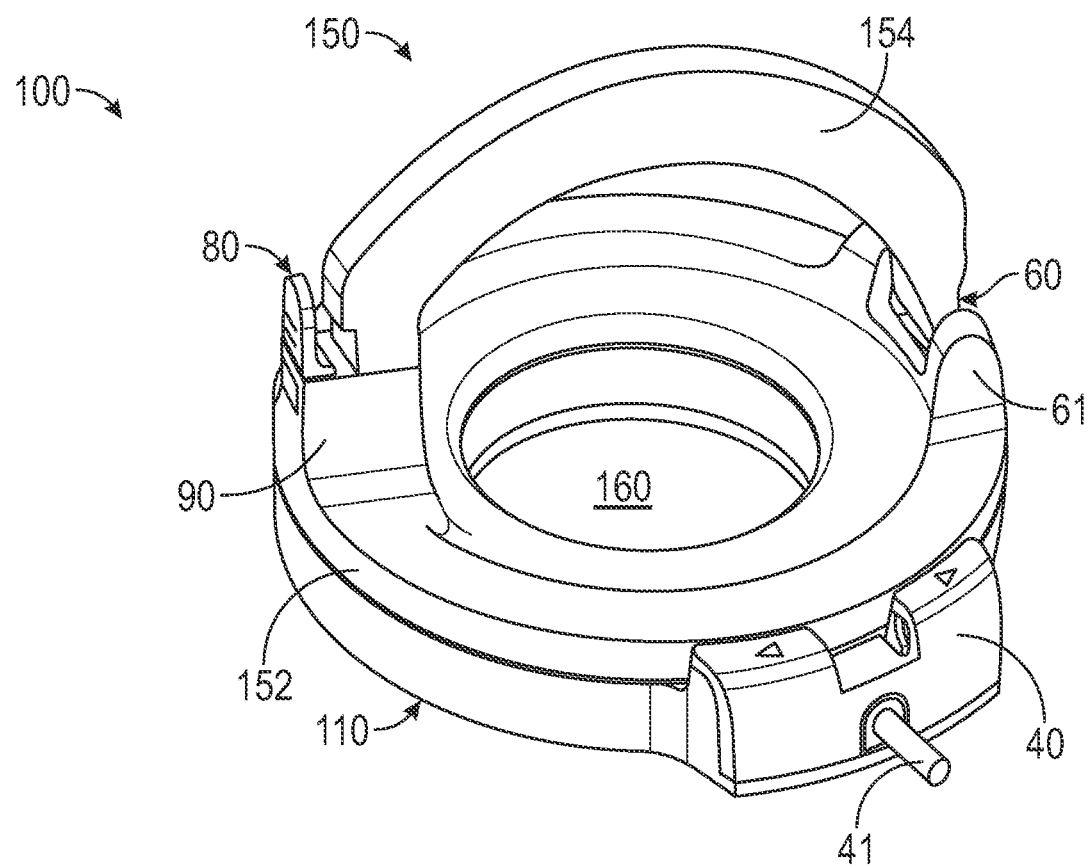
FIG. 21A shows a perspective view of the medical guidance apparatus (without the probe holder)
Figure 21B:
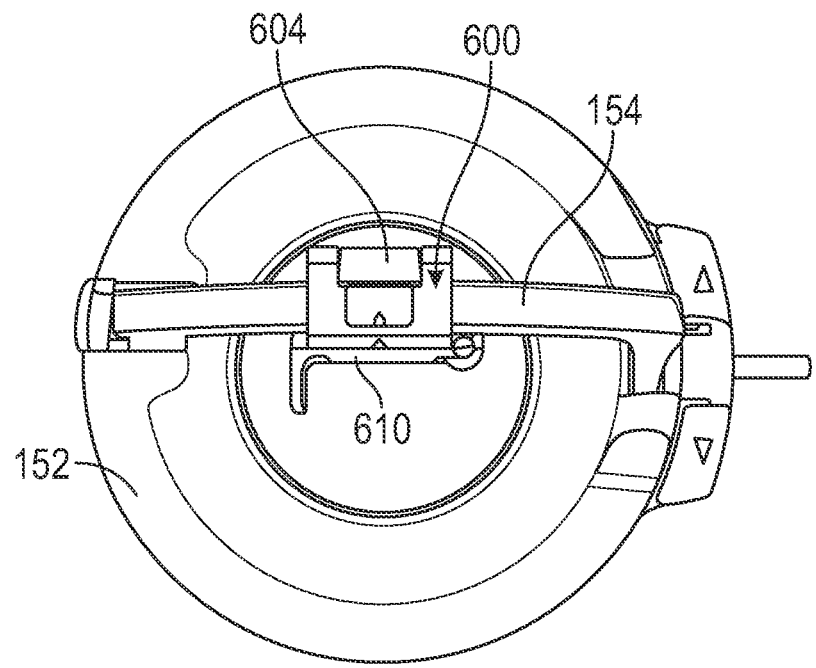
FIG. 21B shows a top view of probe holder mounted on the medical guidance apparatus.

FIG. 21A shows a perspective view of the medical guidance apparatus 100 without the probe holder 600. FIG. 21B shows a top view of the medical guidance apparatus 100 with the probe holder 600 mounted on the arc member 154 of guide 150. The views of FIGS. 21A and 21B show the medical guidance apparatus 100 in a closed or locked state.

As in previous illustrations, the medical guidance apparatus 100 is composed of the base assembly 110 and the guide 150. The base assembly 110 is adapted for mounting the device onto a patient (not illustrated), and the guide 150 is configured to have at least two degrees of freedom adapted for guiding the needle-like instrument to an area of interest inside the patient. In one embodiment, the medical guidance apparatus 100 is a needle guide device configured to be placed on the surface (skin) of a patient's body so that a needle-like instrument can be inserted through a needle entry point on the skin of the patient, via an opening 160. To that end, the medical guidance apparatus 100 is first fixed to the patient with straps or belts (refer to FIG. 27B); thereafter, the needle-like instrument 100 is mounted on the arc member 154, and the needle-like instrument is automatically (or manually) guided to the target area of interest using the navigation software 4116, as described above. In some embodiments, the base assembly 110 may be attached to the patient's skin with adhesive materials (as apposed to belts), as explained above with reference to FIGS. 11-13. A plurality of fiducial markers (not shown) may be included (embedded) in the base assembly 110 and/or the ring 152 to facilitate device-to-image registration.

Figure 22A:
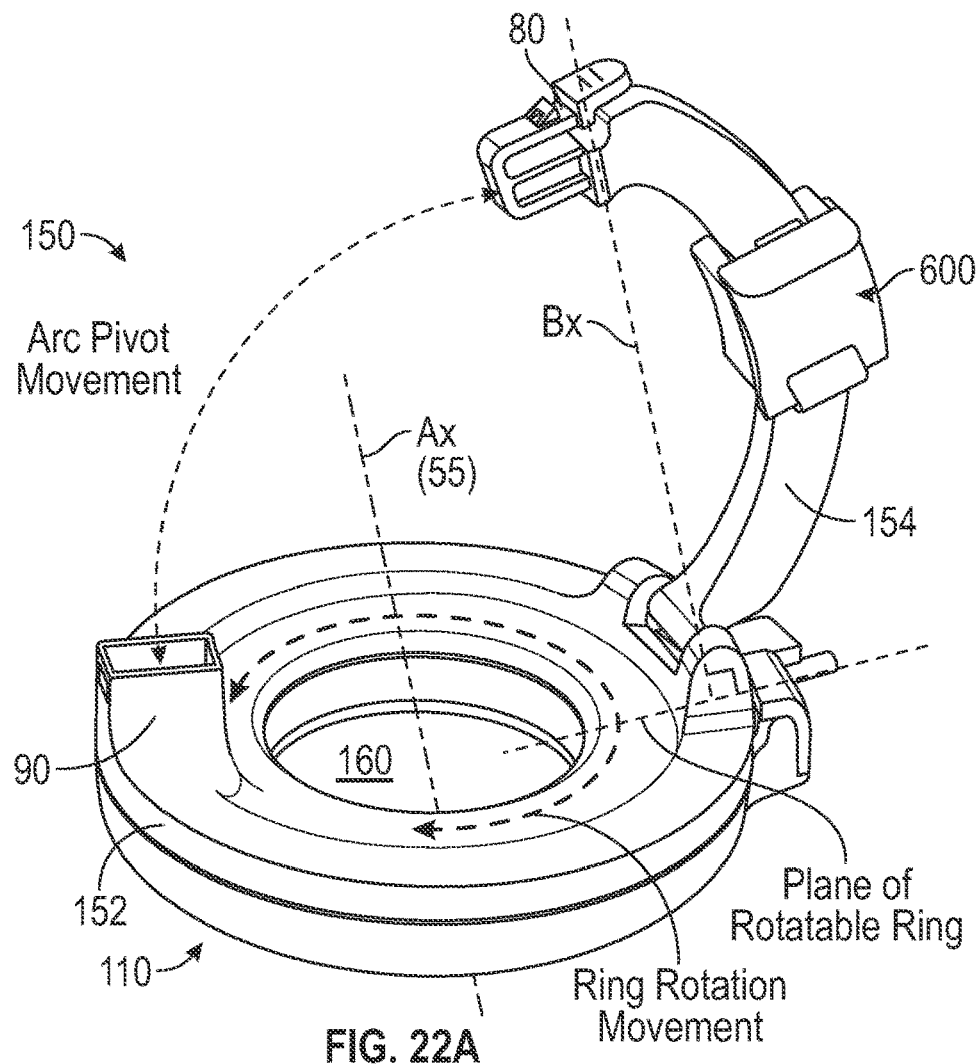
FIG. 22A shows an exemplary embodiment of the medical guidance apparatus 100 with the guide 150 in an open state.

The rotating ring 152 can be fixed at any position thereof to the base assembly 110 using a cam latch mechanism (40, 41). The arc member 154 (arc shaped guide) is hinged on one end thereof (first end 162) to the ring 152 via a pivotable hinge mechanism 60, and on the other end (second end 164) the arc 154 is snap-fitted onto the ring 152 via a snap joint locking mechanism 80. In one embodiment, the pivotable hinge mechanism 60 is a c-shaped hinge that can be pressure-clipped onto a cylindrical pin 64 (see FIGS. 24A-24C), so that the arc member 154 can be pivotable from a closed position (FIG. 21B) to an open position (FIG. 22A). In the open position, the arc member 154 can be rotated 90 degrees or more, such that a line Bx connecting the first end 162 and second end 164 becomes parallel to the rotation axis Ax of the ring 152. Therefore, in a configuration where the arc member 154 is pivoted relative to the rotatable ring 152, the first end and the second end of the arc member 154 can be disposed at a right angle or greater with respect to the plane of the rotatable ring 152, such that the arc member 154 and the probe holder 600 do not interfere with the opening 160 of the base assembly 110. In addition, since the c-shaped hinge can be clipped onto or removed from the cylindrical pin 64, the arc 154 can be fully removed from the ring 152, if necessary. To ensure that the arc shaped guide is rigidly attached to the rotating ring 152, the rotating ring 152 includes a hinge attachment section 61 and an arc support section 90, which are disposed substantially diametrically opposite to each other. As shown in more detail in FIGS. 23A-23C and FIGS. 24A-24C, both the hinge attachment section 61 and arc support section 90 are reinforced by rounded bottom gussets 63 and 93, respectively.

Figure 22B:
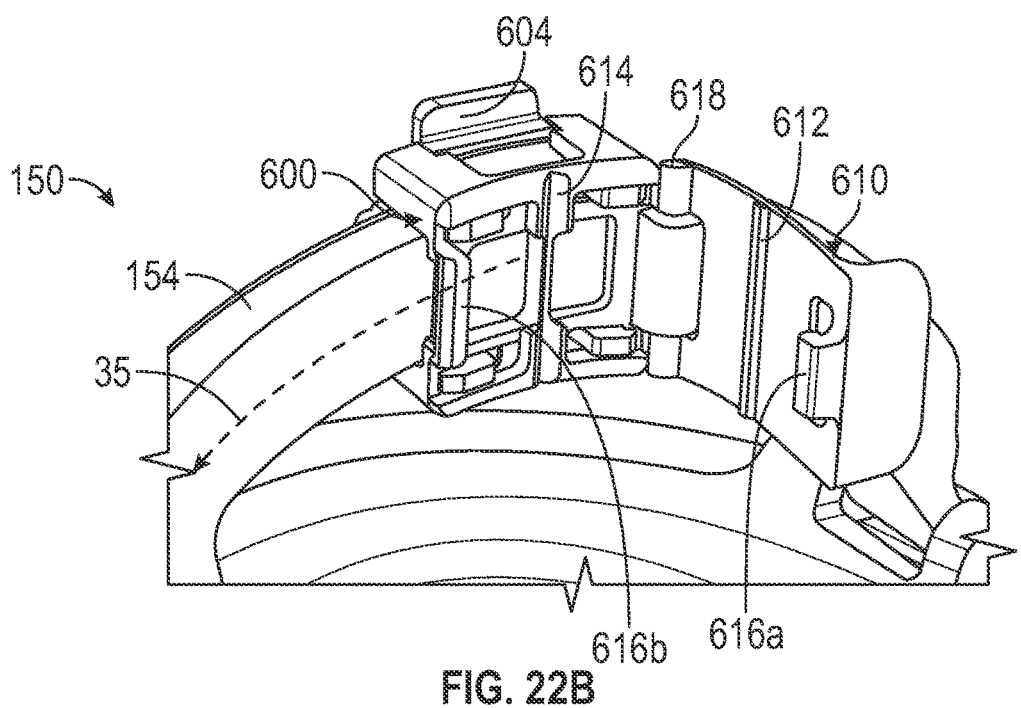
FIG. 22B shows a detailed perspective view of the probe holder 600 in an open state.

FIG. 22B shows a detailed view of the probe holder 600 mounted on the arc member 154. The probe holder 600 includes a probe holder lock 604 and the door 610. A non-illustrated needle-like instrument (probe) is arranged in a probe channel or groove (614, 612) formed in the door 610 of probe holder 600. The probe holder 600 slides along the arc 154 in an arcuate path 35 and can be fixed at any given location along the arc 154 using the probe holder lock 604. The probe holder gate or door 610 swings around a hinge 618. The probe holder gate or door 610 includes a snap joint lock 616 (616a 616b), or the door 610 may include a spring release hinge or snap latch hinge to secure the needle-like instrument in the probe channel or groove (612 614). The latch hinge or spring release hinge (lock 616) can have a spring-loaded plate or handle, which pushes the door 610 against the arc member 154 to secure needle-like instruments of different thicknesses in groove (612 614), and serves to pull the door 610 away from the arc member 154 to release the needle-like instrument from the probe holder 600. In alternative embodiments, the door 610 can be attached to the probe holder 600 with one or more set screws, which can be adjustable to push door 610 against the arc member 154 to secure needle-like instruments of different thicknesses in groove (612 614). In this manner, the door 610 may be configured to hold a needle-like instrument against the groove 614 with an adjustable holding force, as further described below with reference to FIG. 28A.

In one embodiment, the opening 160 of the base assembly 110 is substantially cylindrical and has about 50 millimeters (mm) in diameter. When the arc member 154 is attached at the first and second ends (162, 164) onto the rotating ring 152, the arc member 154 forms a semicircular aperture underneath the inner surface of the arc. In one embodiment, when the guidance apparatus 100 is closed (in a closed state), the arc member 154 and rotating ring 152 form a semicircular aperture of approximately 50 mm between the upper surface of the ring 152 and the highest point on the inner (lower) surface of the arc member 154. As used herein, the term arc or arc member (or arc shaped guide) refers to any portion (other than the entire curve) of the circumference of a circle having a given diameter. Arc length is the distance along the curved line making up outer surface of the arc. Therefore, for example, to form the semicircular aperture of approximately 50 mm, the arc length of arc member 154 refers to a half circumference of a circle having a 50 mm radius, but any portion (other than the entire curve) of the circumference of a circle having a diameter of 100 mm may also be applicable. In some embodiments (FIGS. 22A, 27A, 27B), the arc member is shown as a half circumference, while in other embodiments, (FIGS. 26A-26C) the arc member is shown as a quarter circumference. However, if the diameter of the inner circumference of the arc member is 100 mm, when the arc member 154 is attached to the rotating ring 152, the arc member 154 forms an aperture of 50 mm underneath the inner surface of the arc.

In one embodiment, a rotary encoder (16 in FIG. 24C) is used to measure a position of the rotatable ring 152 with respect to the base assembly 110. In addition, a circuit board and a microcontroller (12 in FIG. 24C) may be provided to process the signals from the rotary encoder 16. To facilitate rotation of the ring 152 with respect to base assembly 110, ball bearings 14 and 15 may be provided. The rotary encoder 16, circuit board and microcontroller 12 may be provided on a base plate 20 of the base assembly 110, and these elements may be covered at least partially by a support or housing 21 of the rotatable ring 152.

Figures 24A, 24B:
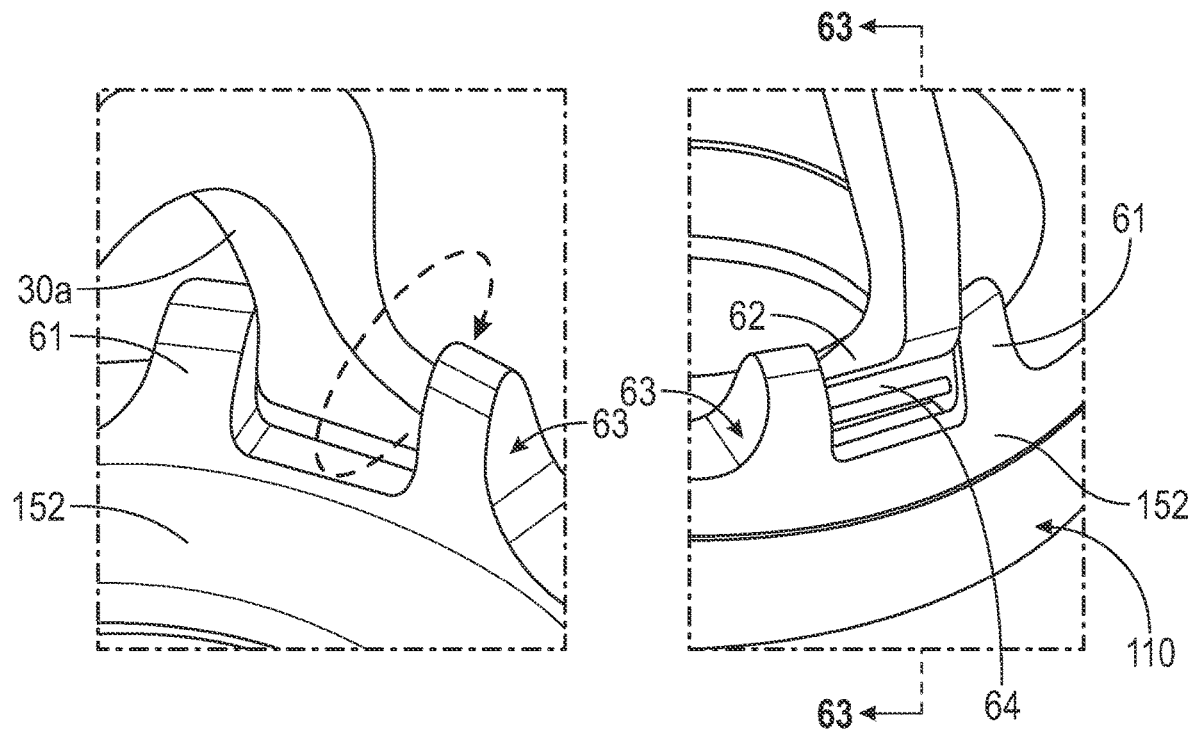
FIGS. 24A, 24B, and 24C are detailed exemplary illustrations of a pivotable hinge mechanism to show a first end of the arc 30 pivotably attached to the rotating ring 152.
Figure 24C:
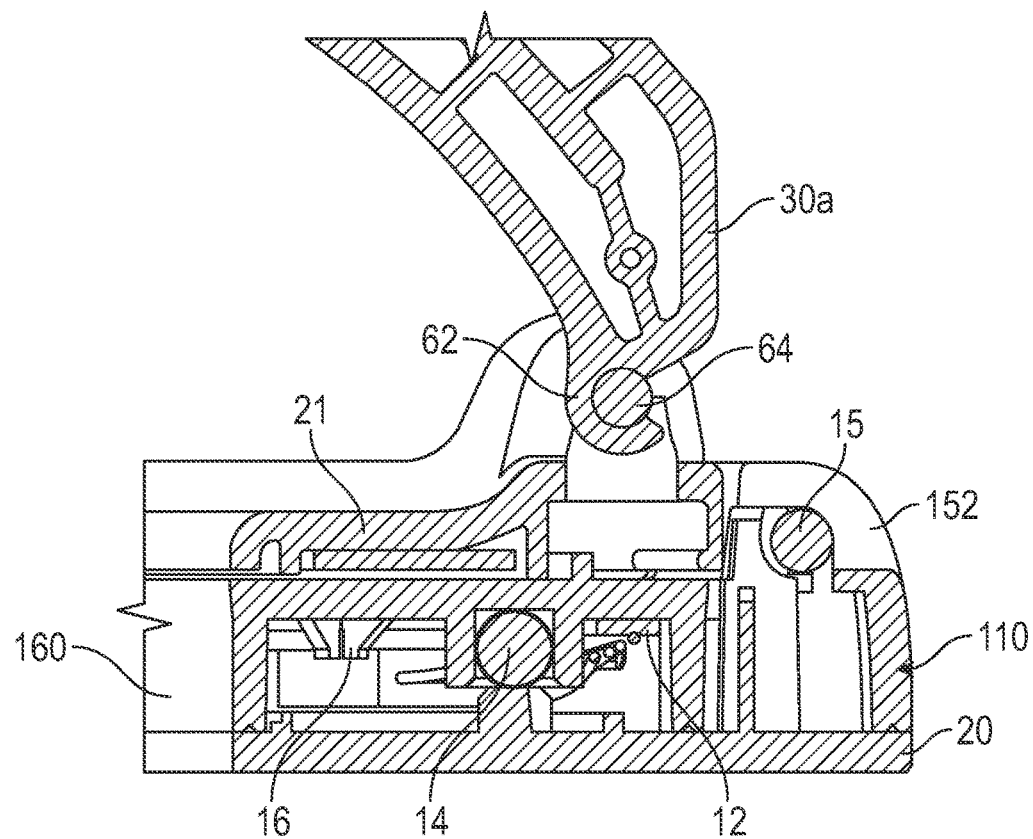

FIG. 22A shows an exemplary embodiment of the medical guidance apparatus 100 in an open state (opened position). In this configuration the second end 164 of the arc member 154 has been un-clipped from the rotating ring 152 and the entire arc member 154, including the probe holder 600, is removed out of the instrument-insertion path 55 which coincides with the axis Ax. In the open position, the arc member 154 can be positioned substantially perpendicular to a plane of the ring 152 or the base assembly 110. However, if more space is needed for accessing to the area of interest on the patient, the first end 162 of arc member 154 can also be detached at the pivotable hinge mechanism 60. To that end, the pivotable hinge mechanism 60 can be designed in a C-shape as shown in FIGS. 24A-24C. This design allows the medical guidance apparatus 100 (guidance system) to be used according to the numerous requirements of a variety of interventional procedures.

For example, during a needle insertion procedure, it is highly advantageous that the arc member 154 is rigidly attached at both ends thereof to the ring 152, as shown in FIG. 21B. However, either before or after the needle insertion procedure, the arc member 154 can be entirely separated (removed) from the ring 152 to allow easier access to areas of interest on the patient. As mentioned above, the based assembly 110 is configured to be strapped or attached onto the patient's body to avoid accidental movement. Therefore, at the beginning of a procedure, only the base assembly 110 and the ring 152 may be attached to the patient's body to give the user (physician) the opportunity to arrange the guidance apparatus 100 on the precise location of needle insertion.

On the other hand, after a needle insertion procedure is completed, e.g., after a first needle has been inserted into an area of interest, the physician may need to access the insertion point for inspection or confirmation. In that case, the arc member 154 can be unlocked from the ring 152 by operating the snap joint locking mechanism 80, and then the arc 154 can be pivotably rotated to the position shown in FIG. 22A. This gives access to the physician for the necessary observation and confirmation of needle insertion. In addition, if more room is necessary for accessing to the insertion area of interest, the hinge mechanism 60 can be disengaged from the hinge attachment section 61 of ring 152 so that the entire arc member 154 and needle holder 600 can be removed from the ring 152. However, even after the arc member 154 and needle holder 600 are removed, the base assembly 110 and ring 152 will remain rigidly attached to the patient's body. To avoid rotation of the ring 152 with respect to base assembly 110, the latch cam 40 is provided at any position along the circumference of ring 152 to maintain the ring 152 in a fixed (non-rotating) position.

Therefore, in the event that a new needle-insertion procedure needs to be performed on the patient, e.g., in the case of having to use multiple needle-like instruments, the arc member 154 including the needle holder 600 can be simply mounted back onto the ring 152 by engaging the pivotable hinge mechanism 60 and click-mounting the arc locking mechanism 80. In this manner, this pivotable and removable arc member 154 and needle holder 600 can provide (i) ease of access to the area of interest, (ii) stiff and rigid support for needle-like instrument insertion, (iii) precise guidance during instrument insertion, and (iv) effective repeatability of insertion because the base assembly 110 and ring 152 can remain rigidly attached to the patient's body at all times during an interventional procedure.

Figure 23A:
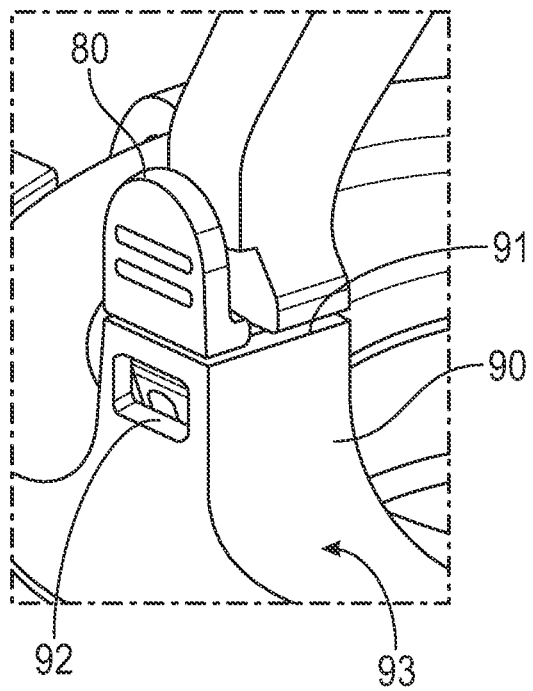
FIGS. 23A, 23B, and 23C are detailed exemplary illustrations of a snap-fit latching mechanism to show a second end of the arc 30 attached to the rotating ring 152.

FIGS. 23A through 24C show detailed exemplary illustrations of the various manners in which the arc member 154 can be attached to the rotating ring 152. FIG. 23A shows an exemplary perspective view of the arc locking mechanism 80 in a closed position. FIG. 23B shows a detailed perspective sectioned view of the arc locking mechanism 80 in a closed position, where the side wall or housing of ring 152 is removed. FIGS. 23A, 23B, and 23C show the arc locking mechanism 80 is a snap joint (or clip) type mechanism. Snap joints are a very simple, economical and rapid way of joining two different components. Most types of snap joints have in common the principle that a protruding part of one component, e.g., a hook, stud or bead is deflected briefly during the joining operation and catches in a depression (undercut or indent) in the mating component. In FIGS. 23A-23C the rotating ring 152 includes an arc support section 90 which includes an opening or undercut 92 and a receiving surface 91. The arc locking mechanism 80 includes a hook-shaped clip 82 (U-shaped snap joint) with a protruding part 82a. In this manner, during the operation of joining the arc member 154 to the ring 152, the arc locking mechanism 80 exerts a deflecting force on the hook-shaped clip 82 and the protruding part 82a catches or engages the opening or undercut 92.

After the joining operation, the snap-fit features of locking mechanism 80 and arc support section 90 return to a stress-free condition. The joint between the arc member 154 and the ring 152 is rigid, but separable by applying a force to the locking mechanism 80 to disengage the protruding part 82a from the undercut 92. The force required to separate the components of a snap fit joint varies according to the design and the required load. Snap-fit joints as the locking mechanism 80 are generally implemented using certain polyurethane materials which are known to be rigid and can resist certain amount of stress force. And, in view of their high level of flexibility, plastics are also usually very suitable materials for this joining technique.

Figure 23B:
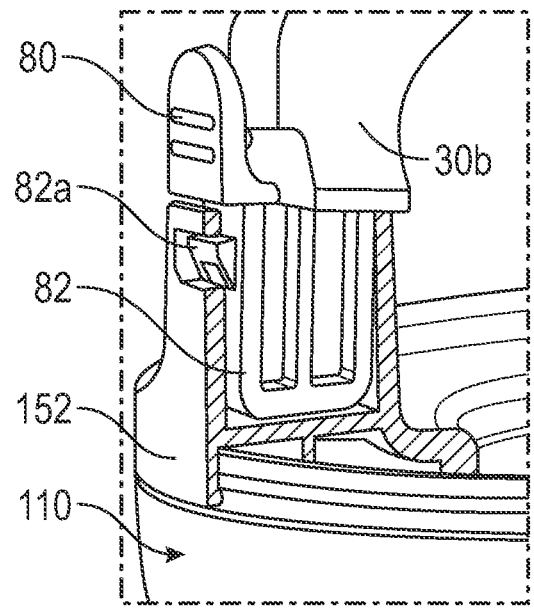
Figure 23C:
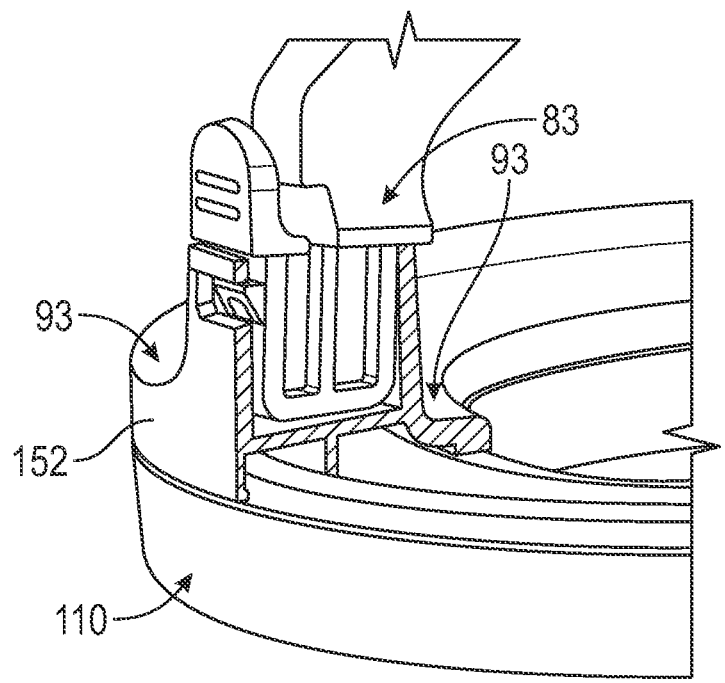

It should be noted that although the hook-shaped clip 82 is described as a U-shaped snap joint, as shown in FIGS. 23B-23C, other design possibilities exists for snap joints. Some known types of snap joints include cantilever snap joints where the load is mainly flexural (U-shaped snap joints are a variation of the cantilever type); torsion snap joints where shear stresses carry the load; and annular snap joints which are generally rotationally symmetrical and involve multiaxial stresses are also available.

Figure 25A:
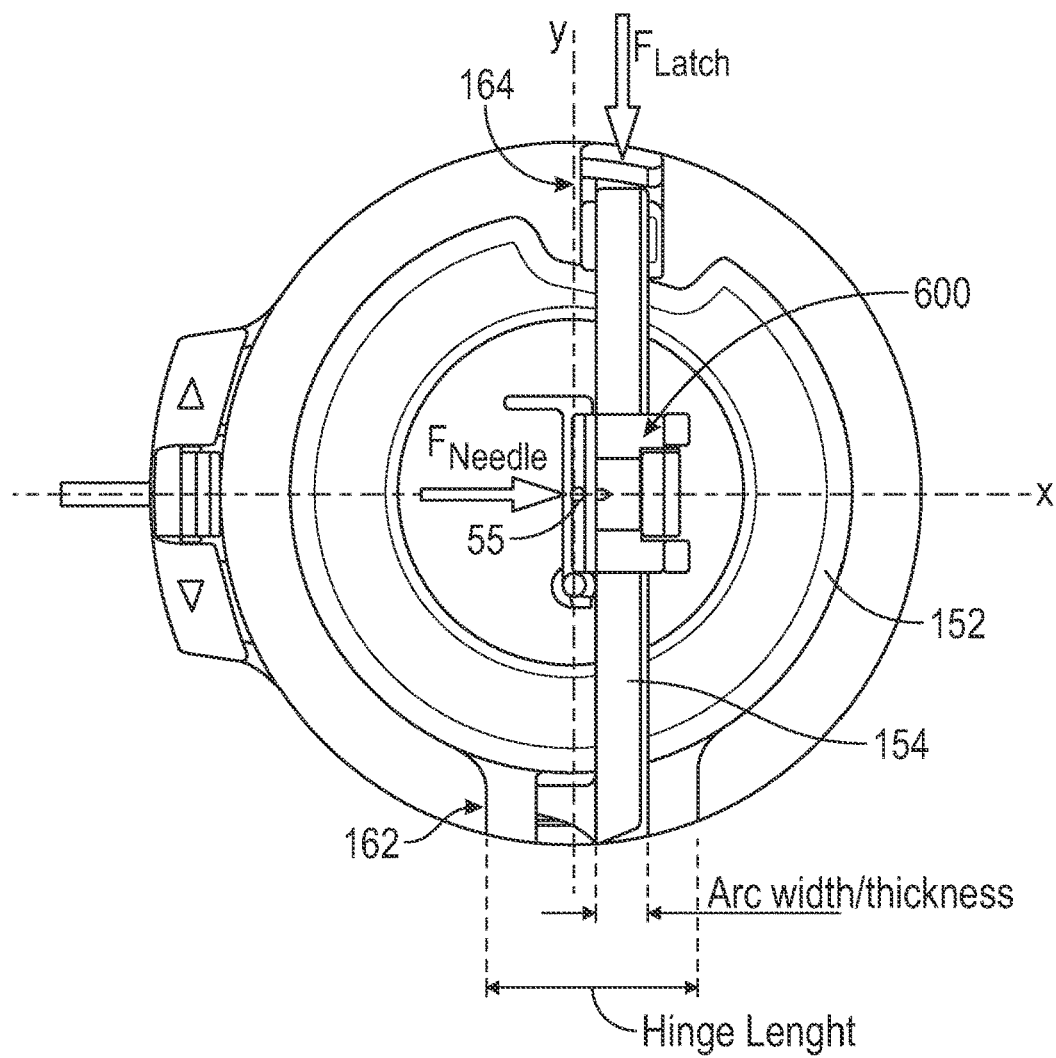
FIG. 25A and FIG. 25B are respectively top and side views of an exemplary medical guidance apparatus 100 illustrating a vector diagram of induced forces by a needle-like instrument and counteracting supportive forces generated by the medical guidance apparatus.
Figure 25B:
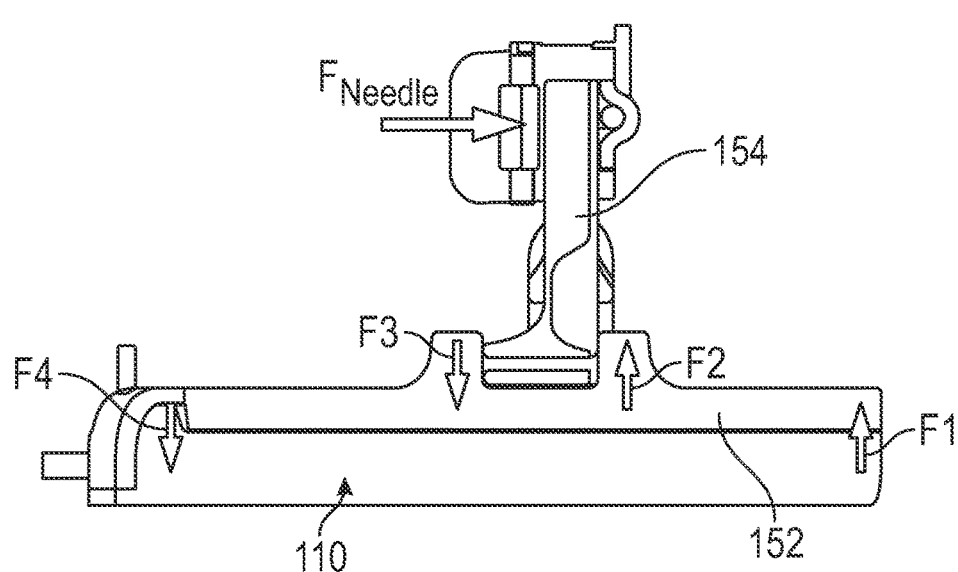

FIGS. 25A and 25B illustrate exemplary forces applicable to the use of snap joints to improve stability of arc member 154 with respect to base assembly 110. In one embodiment of the present disclosure, the cantilevered U-shaped type is used where the latching force ($F_{Latch}$) to open and close (engage and disengage) the locking mechanism is 80 is applied in a direction parallel to the longitudinal direction of the arc member 154. This force $F_{Latch}$ is substantially perpendicular to the load force ($F_{Needle}$) exerted by the needle-like instrument when loaded onto the arc member 154 (refer to FIGS. 25A-25B). In this manner, since the latching force $F_{Latch}$ is perpendicular to the load force $F_{Needle}$, this design allows to minimize torsion of the latching mechanism 80. The arc locking mechanism 80 has a spring-clip to secure the arc member 154 onto the ring 152 in the closed position. The latching direction is intentionally designed to be in the direction along the longitudinal direction of the arc member 154, such that the compliance of the clip mechanism is not added to the compliance of the arc when lateral forces are present when the needle-like instrument is loaded onto the probe holder 600.

FIGS. 24A, 24B, and 24C show one exemplary implementation of the arc's pivotable hinge mechanism 60. FIG. 24A shows the pivotable hinge 60 seen along the inner surface of ring 152. FIG. 24B shows the arc pivotable hinge 60 as seen along the outer surface of the ring 152. The hinging action of the arc member 154 is accomplished using a c-clip style hinge interface which pivots around a pin 64. Specifically, a stiff pin 24 is integrated into an arc supporting section 61 of the rotating ring 152. The arc member 154 is terminated at its first end 162 with the complimentary c-clip 62 to go over the pin 64. The diameter of the pin 64, direction of the hinge, and the dimensions of the hinge all contribute to the stiffness of the design to obtain a solid and rigid support for the arc member 154. FIG. 24C shows a cross-sectional view, along lines 63-63 of FIG. 24B, showing parts of the pivotable hinge 60 and the base assembly 110. As shown in FIG. 24C, first end 162 of arc member 154 has a c-shaped hinge 62 that can be snap pressed onto the pin 64. The base assembly 110 includes a base plate 20, top plate 21, and a cylindrical opening 160 connecting the top and bottom plates.

FIG. 25A and FIG. 25B are top and side views of the medical guidance apparatus 100 illustrating a vector diagram of induced forces by a needle-like instrument, when mounted onto arc member 154, and the counteracting supportive forces generated by the joint of the ring 152 to the arc member 154. Notably, as described above, the arc member 154 can be rigidly attached to the rotating ring 152, at the first end 162, by the hinge mechanism 60 and, at the second end 164, by the spring clip of locking mechanism 80. The portion of the arc member 154 that inserts the spring clip mechanism into the arc support section 90 is tightly held on either side by the flat receiving surface 91 of rotating ring 152. This tightly held joint, prevents the arc member 154 from inclining or tipping laterally. As shown in FIG. 25A, the arc member 154 is disposed substantially diametrically across the rotating ring 152. However, to provide stability, the center of the opening 160 (i.e., the axis Ax of the cylindrical opening) substantially coincides with the instrument insertion path 55 when the needle or probe is perpendicular to the ring 152. Moreover, even when the probe holder 600 slides on the arc member 154 along the arcuate path 35 and the ring 152 rotates around the axis Ax, the insertion path 55 still intersects the axis Ax of the cylindrical opening 160 at the bottom surface of the base assembly 110 (refer to FIG. 4). In this manner, the guidance apparatus 100 is said to have remote center of motion (RCM) at approximately the insertion point.

Additionally, in terms of dimensions, at the first end 162, the hinge length is significantly larger than the width (thickness) of the arc member 154, creating a large moment arm to resist lateral forces ($F_{needle}$) applied to the arc member 154 when the instrument is mounted thereof. The c-clip style of the pivotable hinge 60 is configured to remove any diametrical tolerance between the pin 64 and the c-clip hinge, and to rigidly secure the arc member 154 to the rotating ring 152. The result of these design aspects is that the arc member 154 becomes rigidly and securely attached to the rotating ring 152. When forces ($F_{needle}$) are applied on the arc member 154, for example, during an interventional procedure, the forces are transmitted through the arc member 154 to the rotating ring 152. Because of the manner in which the arch member 154 is joined to the rotating ring 152 and the base assembly 110, the applied forces ($F_{needle}$) are distributed throughout the base assembly 110 as forces F1, F2, F3 and F4. Forces F1-F2 are the counteracting supportive forces generated by the design of the guidance apparatus 100. That is, because there is such a rigid connection between the two bodies (arc member 154 and rotating ring 152), the forces applied the arc member 154 are transmitted to the entire area of the rotating ring 152 and the base assembly 110. In this manner, the moment or torque is applied first to the mounting features (hinge and clip) of the arc member 154 to the movable ring, and then distributed through the ring 152 to the base assembly 110. This significantly improves upon known guide devices where stiffness of the arc to the base, as well as the possibility of easily removing the arc from the base was not provided.

Figure 26A:
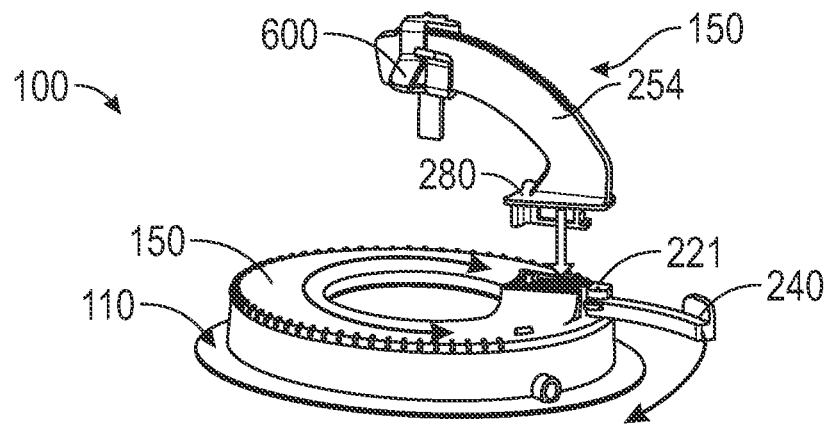
FIGS. 26A, 26B, and 26C illustrate various views of a further embodiment of a medical guidance apparatus having a removable arc guide.
Figure 26B:
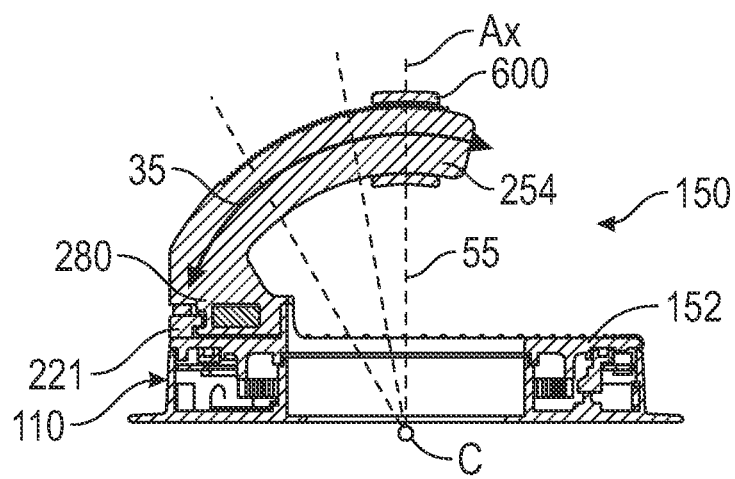
Figure 26C:
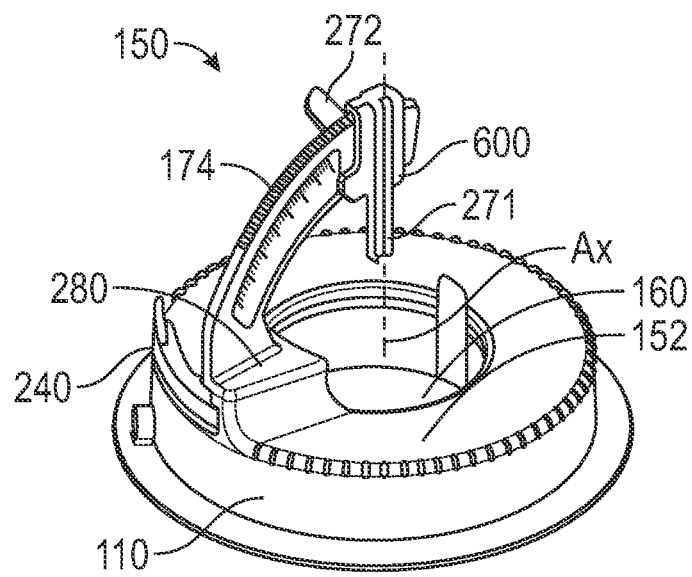

FIGS. 26A, 26B, and 26C illustrate a further exemplary embodiment of a medical guidance apparatus 100 having a removable arc shaped guide. FIG. 26A shows the guidance apparatus 100 with an arc member 254 in a detached state. FIG. 26B shows a cross-sectional view of the guidance apparatus 100. FIG. 26C shows a perspective view of the guidance apparatus 100 in an assembled or attached state. In this embodiment, to provide further accessibility to the area of interest on the subject, the arc member 254 includes an arc where only one end thereof (the first end) is releasably attached to the rotating ring 152. Similar to the previous embodiments, the guidance apparatus 100 includes a base assembly 110, a rotating ring 152, an arc 254, and a probe holder 600. The base assembly 110 includes an opening 160 which is substantially cylindrical similar to the previous embodiments.

Figure 27A:
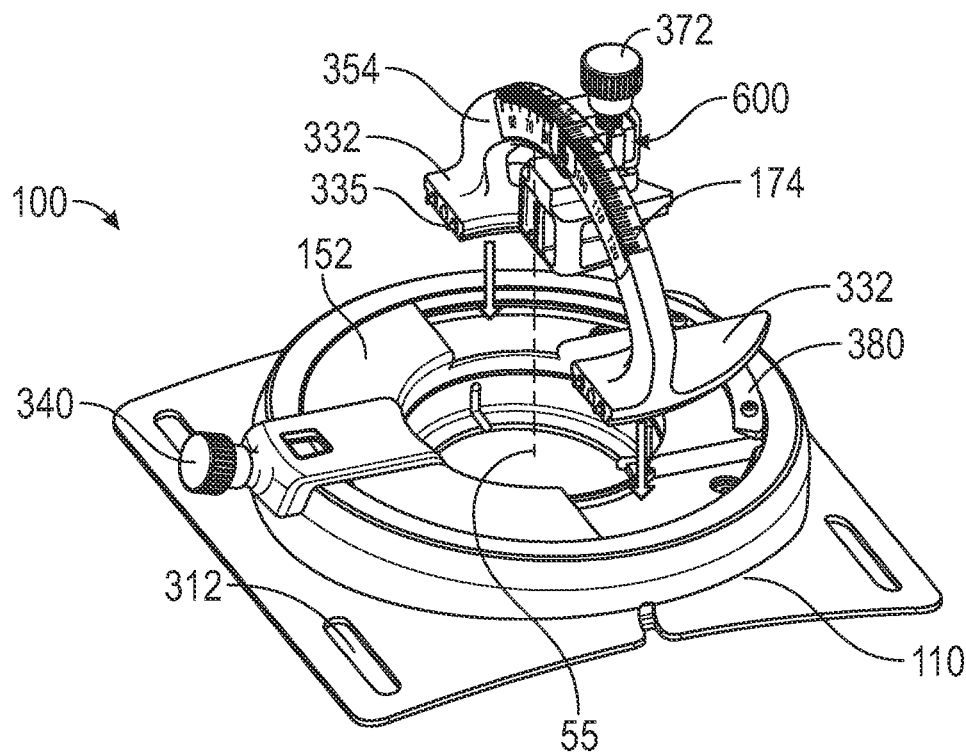
FIGS. 27A and 27B illustrate opened and closed states of yet another embodiment of a medical guidance apparatus having a removable arc guide.
Figure 27B:
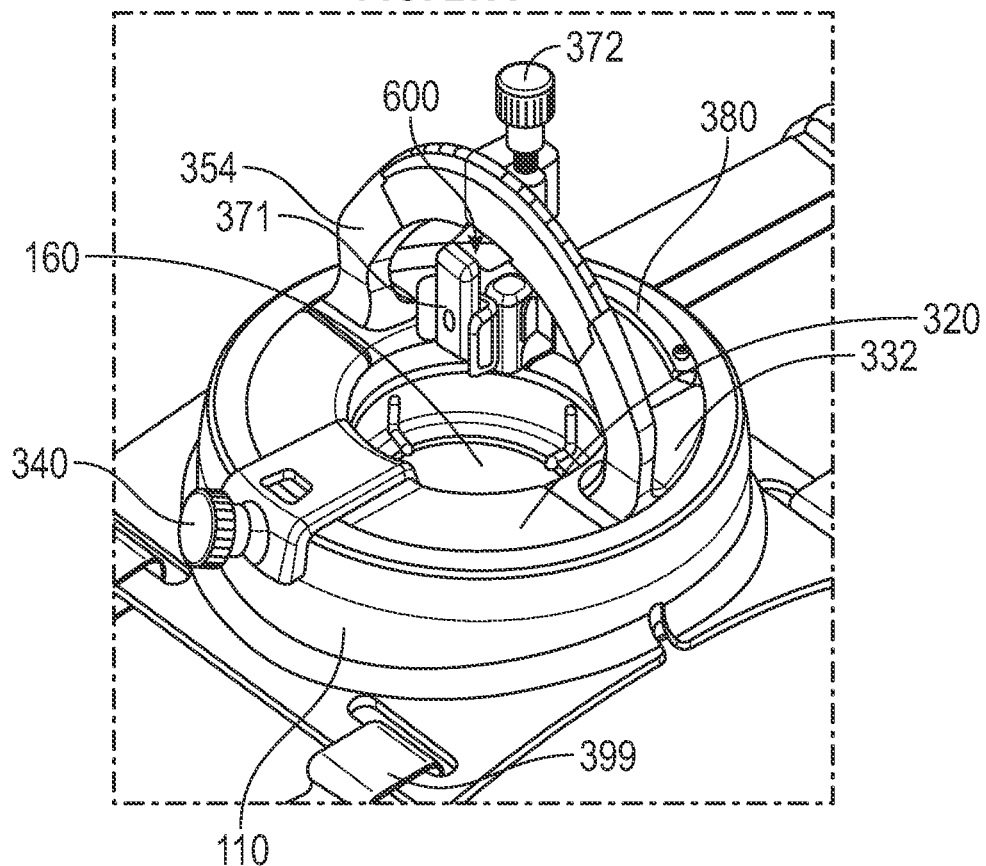

The rotating ring 152 includes a quick-lock base 221 (arc support section) and a quick-lock lever 240. The probe holder 600 includes a probe holder lock 272 and a probe channel 271. In this embodiment, the removable arc member 254 makes use of a cam lever locking mechanism for easy assembly and disassembly. When the quick-lock lever 240 is opened, the arc base 280 is inserted into the rotating ring support section 221. When the quick-lock lever 240 is closed, as shown in FIG. 26C, the arc member 254 is locked and held rigidly in place by a cam lock mechanism. The needle channel 271 is preferably directed to cross with the center (axis Ax) of the cylindrical opening 160 at the bottom surface of the base assembly 110. In this manner, an insertion path 55 intersects the cylindrical axis (axis Ax of the opening 160) at a point C at the bottom plane of the base assembly 110 regardless of the position of the needle holder 600 along the arc member 254. As shown in FIG. 26C, the arc member 254 includes angular reference marks 174 along one or more surfaces of the arc member. Therefore, the arc member 254 effectively acts as a protractor assembly for accurately guiding a needle-like instrument along an insertion angle FIGS. 27A and 27B illustrate yet another exemplary embodiment of a guidance apparatus 100 having a removable arc member 354 (arc shaped guide), a rotating ring 152, and base assembly 110. Similar to the other embodiments, the guidance apparatus 100 includes the base assembly 110 with an opening 160, the rotatable ring 152, and arc member 354 configured to hold and guide a probe holder 600. In this embodiment, the arc member 354 connects to the rotating ring 354 at first and second ends, and the arc member 354 disconnects entirely from the rotating ring 152 by the action of spring loaded pins. More specifically, on the arc member 354 there are support sections 332 at each end thereof which act as 'feet' that interface with the rotating ring 152 in three ways: (a) the feet are inset into the rotating ring 152 such that they are constrained in all but the vertical direction, (b) the tips of the feet are inserted underneath a restraining bar 380 which prevents the feet from rotating out of the inset, and (c) spring-loaded pins 335 are provided on the flat edge of the feet 332 to interface with the rotating ring 152 such that the spring force of the pins pulls the arc member 354 down against the rotating ring 152 to ensure a rigid and secure connection between the ring 152 and the arc member 354. The probe holder 600 includes a probe/needle lock 371 and a probe holder lock 372 which servers to lock the probe holder 600 onto the arc member 354 at a desired insertion angle. Angular reference marks 174 on the surface of arc member 354 allow for the user to have a reference of the angle of insertion. In addition, a locking mechanism 340 is provided to lock the rotating ring 152 with respect to the base assembly 110 at a given position. The base assembly 110 is provided with openings 312 which serve to attach the guidance instrument 100 to the body of a patient using straps or belts 399 (shown in FIG. 27B).

Probe Holder for Multiple Probes

The previous embodiments have shown the probe holder 600 configured to hold a needle-like instrument of different sizes and diameters. As explained above, the probe holder 600 can be used to place one or more probes in a target area of a subject by individually guiding such probes, e.g., 17-, 14-, and 13-gauge cryoprobes, in a process known as single-probe ablation. However, the simultaneous use of multiple probes in parallel, e.g., for multi-probe ablation, is also possible.

FIGS. 28A through 28C show an embodiment of a probe holder 600 configured for multi-probe use. FIG. 28A shows the probe holder 600 configured to simultaneously hold a plurality of needle-like instruments of different sizes and diameters for example, ablation probes in a gauge range of 18 to 13 can be used. The probe holder 600 is secured to the arc member 154 with a cam lock mechanism similar to the previous embodiments; in FIG. 28A, the locking lever 604 of a cam lock mechanism is shown in a locked position. In this embodiment, the probe holder 600 includes a first door 610a and a second door 610b respectively affixed to the probe holder 600 by a corresponding securing mechanism, such as a first set screw 626a and second set screw 626b. The probe holder 600 is mounted onto the arc member 154, and is configured to move along an arcuate path 35 defined by the shape of arc member 154. Similar to other embodiments, the arc member 154 includes angular reference marks 174 along at least part of one or more surfaces thereof.

A plurality of grooves 614a, 614b, and 614c are formed on surfaces of the probe holder 600. The probe holder 600 includes a plurality of doors (610a 610b) configured to be separately secured against the surfaces of the probe holder where the grooves are formed. In FIG. 28A, a first door 610a includes two tabs or notches (or grooves) which match the two grooves (a first grove 614a and a second grove 614b) formed on a first surface of the probe holder 600. In this manner, the combination of the first door 610a and a first surface of the probe holder 600 forms two channels for securing therein a corresponding pair of first and second probes (not shown). A second door 610b includes one tab or notch (or groove) which matches a third groove 614c formed on a second surface of the probe holder 600. The combination of the second door 610b and the second surface of probe holder 600 forms a third channel for securing therein a third probe (not shown). The doors 610a and 610b can be tightened and loosened separately by using each designated set screw. Each door and set screw pair is designed in such a way that even when loosened to its maximum adjustment level, the door still stays attached to the probe holder 600. The adjustability of the doors by the set screws allows the user to securely fix in place probes of different size, or to have each probe with a certain degree of slack (loosen) to safely slide freely while being guided to any depth based on the user preference. In other words, each adjusting mechanism (set screw or the like) is configured to hold one door among the plurality of doors (610a, 610b) with respect to the probe holder 600 with an adjustable holding force.

To better control the depth of probe insertion, the top surface of the probe holder 600 is made flat such that the top surface of the probe holder 600 is perpendicular to each probe channel. In this manner, if three (3) probes are inserted, the three probes will be parallel to each other, and all probes could be inserted the same depth to have the tips of the probes at the same distance along the trajectory which is a desired configuration for multi-probe ablations.

In this embodiment, the probe holder 600 is substantially wider than a probe holder for single-probe ablation. In the embodiment of FIG. 28A, the probe holder is wider not only to accommodate a plurality of probes, but also to accommodate the set screws. Having the probe holder 600 with a wider design has the advantage of making the probe holder more stable on the arc due to the wider stance. One additional benefit of a wider probe holder is that the doors provide adjustable holding force (i.e., the user can tighten or loosen the set screws to the desired force).

In some embodiments, the probe holder 600 is not removable from the arc member 154. The arc member, however, is removable from the base assembly 110. The reason this features exists is that it is roughly 6 cm from the top of the arc to the bottom of the device. When inserting a 15 cm probe, this would eliminate 6 cm from possible insertion depths (i.e. depths greater than 9 cm couldn't be achieved). However, by making the probes able to released from their guiding channels and making the arc removable the physician can release a partially inserted needle, remove the arc member 154, and push the needle further, e.g., under image guidance. Therefore, it is possible to reach depths greater than 9 cm.

The shape of each groove of the probe holder is designed so as to permit the usage of multiple needle gauges. In some embodiments, all grooves may have the same shape, e.g., a "v" shaped groove or a "c" shaped groove, but the depth and/or width of each groove may be different from each other. Also, in some embodiments, each groove may have a different shape (i.e., a different cross-section) so as to fit a different medical tool in each groove. Moreover, as the spacing between the door and the probe holder increases by loosening the set screw, so does the maximum diameter of a probe which can be inserted through the grooves. In this manner, different probes or other needle-like instruments, or combinations thereof, can be used simultaneously with the probe holder 600 of FIG. 28A.

FIG. 28B shows an exemplary arrangement of a plurality of probes P1, P2, and P3 which can be mounted in corresponding grooves 614a, 614b, and 614c of the multi-probe holder 600 of FIG. 28A. Naturally, the arrangement, number, size, shape, etc., of the grooves is not limited to those illustrated in FIGS. 28A and 28B. In addition, the number of doors and set screws can also be modified such that, for example, each groove can have a corresponding pair of a door and set screw, so that each probe can be individually manipulated. FIG. 28C shows the probe holder 600 having its top surface thereof flat and perpendicular to the channel of each probe P1, P2. The probe holder 600 is configured to move (slide) along the arc member 154 in an arcuate path 35. To more precisely monitor and control the depth of needle insertion, the top surface of needle holder 600 can be designed to be tangential to the outer surface (highest point) of the arc member 154. Therefore, regardless of the angle of insertion, the probes can be maintained parallel to each other, and the depth of insertion can be measured from the flat surface.

Improved Stability for Needle Placement

The combination of the base assembly 110 and the guide 150 in each of the foregoing amendments provide advantageous benefits of improved stability and ease of access to areas of interest through the opening 160. In the guidance apparatus illustrated in FIGS. 1-4, the tapered design of the base assembly 110 and taper portions 130 and 180 can be understood as a conical interface, where the base assembly 110 and guide 150 are geometrically aligned at the taper portions 130, 180 to the center axis of the conical interface. Kinematically, this interface eliminates in-plane relative motion between the base assembly 110 and guide 150 while allowing the guide 150 to rotate with increased stability. In the embodiment shown in FIGS. 8, 9, and 10, the arc member 1154, 2154 may be integrally formed with the ring frame ring 1152, 2152 such that the entire guide 1150, 2150 is monolithically formed, as with the guide 150 of FIGS. 1-4. Thus, the guide 2150 has the same structural advantage as noted above with the guide 150.

In the case of inserting more than one needle-like instrument using one of the guidance apparatuses illustrated in FIGS. 1-10, the operator must release the previous needle-like instrument from the probe holder to initiate insertion of a new needle-like instrument. However, in this process, once one or more of the needle-like instruments have been inserted, the operator may decouple the guide 150 from the moveable ring of the base assembly 110. And, once the guide 150 has been decoupled from the base assembly, the operator can freely lift the guide 150 away from the insertion path for, for example, confirming needle insertion. Further, the operator may decouple and re-orient the guide 150 such that each needle-like instrument passes through the desired insertion point. Thus, it is advantageous that in in at least some embodiments the guide 150 is completely removable from the procedure site, even when the needle-like instrument is still tethered, such as for percutaneous ablation probes.

In the various embodiments shown in FIGS. 20 though 27B, the detachable arc member 154 improves on the benefits of having a monolithic arc/ring design, without eliminating the benefits of having a removable arc. The medical guidance apparatus 100 disclosed herein provides a very rigid guide by using the needle holder with the arc-shaped guide and the closed-frame structure. Therefore, the guidance apparatus can guide the medical tool to the target position along the planned trajectory precisely, and can provide immediate access to the target area by removing at least part of the guiding part (guide 150), while maintaining the base assembly fixed to the patient's surface.

Also, in at least some embodiments, the probe holder can be attached and detached from the movable structure even after the medical tool is inserted by using the space in the first part of the circumference. By detaching the needle guide, the physician can use the main opening to give necessary treatments to the patient and can avoid a potential obstacle for the inserted needle without dislocating the ring and base of the device. Besides that, the medical guidance apparatus has only one mechanical interface between the movable ring and the needle guide, and can provide minimal assembly steps to detach and attach the needle guide. Therefore, the medical guidance apparatus can increase efficiency of the intervention and decrease positional errors and human factor errors caused by assembly.

Improving Visibility of Area of Interest

In terms of visibility and access, the arc member can be removed entirely from the insertion point or surgical area, if needed, by unclipping the arc from the rotating ring, or by removing the entire monolithic guide (arc and rotating ring). With the arc still installed (monolithically built or hinged onto the ring) but open on one end, the guide 150 can be moved out of the insertion path to provide sufficient access to the insertion point. With the arc installed and closed, the aperture in the base assembly of the device as well as the open design of the arc, can still allow the physician to access the insertion point both visually and manually.

Practical Example

A practical example of a medical guidance apparatus to guide a needle-like instrument (e.g., a needle, ablation probe, or catheter) may include a base assembly including a base-plate opening, and a bottom surface thereof mounted to a patient's body. The base plate may have any shape. However, a circular base shape may be advantageous in some applications; the base outer diameter may be about 50-150 mm; the inner diameter may be about 30-100 mm; the arc member is any portion (other than the entire curve) of the circumference of a circle having a diameter of about 50-150 mm. A minimal height of the base assembly needed to house all electronic components, and provide improved stability may range from about 5 to 25 mm depending on material. The movable or rotatable ring that is attached to the base assembly may rotate entirely, or the movable ring may have two parts including a fixed outer ring and a rotatable inner ring.

The movable (rotatable) ring can be locked at any desired angle with respect to the base assembly. The arc member or arc shaped guide includes integrated mounting features (c-shaped pivotable hinge, latch locking mechanism) used to rigidly attach one or both ends the arc shaped guide to the ring. In some embodiments, the arc member can be monolithically formed with the rotating ring. In this case, the entire guide composed of the rotating ring and arc member can be removable from the base assembly.

Specific dimension requirements (length of hinge greater than arc thickness) provide a stiff base for arc attachment to ring. A needle guide including an arc member fixed on both ends to the ring provides a rigid and stable connection. At the same time, since the arc is hinged on one side and releasably attached on the other, the arc can be pivoted away from the needle insertion path and/or it can be entirely removed from the ring.

Large hinge length relative to arc thickness provides no-slop fit of arc on the hinge, no slop fit between arc and side walls of latch base. A strong hook-shaped clip with latching force perpendicular to load forces allow holding the arc member stably latched onto the ring during mounting and guidance of the probes. Gussets at the base of hinge and latch sections serve to improve cantilevered arc stiffness. The rigid connection between arc member and rotating ring effectively creates a monolithic arc/ring joint. At the same time, the arc can be quickly unlatched and opened up to increase manual and visual accessibility to the insertion area of interest. The arc can be detached from the hinge to allow full access to the insertion site.

A probe holder that is removably attached to the arc-shaped guide is also advantageous. In some embodiments, the probe holder has a latching door to accept and secure an instrument, or release said instrument. The probe holder can slide along the arc, and then can be fixed anywhere along arc to make angle with vertical relative to the base plate or rotating ring. The probe holder can accept a range of instrument diameters from about 0.5-3.5 mm.

When the medical guidance apparatus is implemented as part of an automated (robotic) interventional medical device, the embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., an application specific integrated circuit (ASIC) or a field-programmable gate array (FPGA) board) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/ or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

It should be understood that all non-mutually exclusive features shown and discussed with respect to a specific exemplary embodiment may be applied to all other example embodiments. For example, angular markers may be used in place of illuminators and vice versa for all embodiments, having a different color on the guide surface may be applied to all embodiments, having a grip may be applied to all embodiments, having an adhesive marker may be applied to all embodiments, using an encoder may be applied to all embodiments, using a probe holder for guiding multiple probes may be applied to all embodiments, etc.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A medical guidance apparatus, comprising:
    a base assembly having an inner circumference defining an opening and configured to be attached to a subject; and
    a guide configured to be mated with the base assembly, the guide including:
        a rotatable ring; and
        a removable arc member having a first end and a second end,
    wherein, in a configuration where the guide is mated with the base assembly,
        the opening of the rotatable ring overlays the opening of the base assembly,
        the first end of the removable arc member is removably connected to the rotatable ring and the second end extends diametrically opposite to the first end across the rotatable ring, and
        a probe holder is mounted on the removable arc member so as to hold a needle-like instrument at a desired angle relative to an axis of the rotatable ring.

2. The medical guidance apparatus according to claim 1, wherein the first end of the removable arc member is hingedly attached to the rotatable ring at a first position thereof and the second end of the removable arc member is removably attached to the rotatable ring at a second position thereof, wherein the first position is diametrically opposite to the second position across the rotatable ring.

3. The medical guidance apparatus according to claim 1, further comprising a controller box,
    wherein the controller box is provided outside of the base assembly and in electrical communication with the base assembly.

4. The medical guidance apparatus according to claim 1, wherein the removable arc member comprises a guidance surface, and
    wherein the guidance surface comprises one or more angular reference marks.

5. The medical guidance apparatus according to claim 4, wherein the probe holder includes an indicator configured to enhance viewing of the one or more angular reference marks provided on the guidance surface of the removable arc member.

6. The medical guidance apparatus according to claim 5, wherein the indicator comprises a magnifier for magnification of the one or more angular reference marks formed on the removable arc member guidance surface.

7. The medical guidance apparatus according to claim 1, wherein the probe holder is affixed to the removable arc member by a locking mechanism.

8. The medical guidance apparatus according to claim 1, wherein the probe holder further comprises a groove for accepting therein the needle-like instrument and a door for holding the needle-like instrument in the groove with an adjustable holding force.

9. The medical guidance apparatus according to claim 8, wherein the door is hingedly attached to the probe holder, and
    wherein the door is removable from the probe holder.

10. The medical guidance apparatus according to claim 8, wherein the door includes a tab configured to align with the groove to aid in holding the needle-like instrument therein.

11. The medical guidance apparatus according to claim 1, wherein the probe holder comprises a plurality of grooves for accepting a corresponding plurality of needle-like instruments.

12. The medical guidance apparatus according to claim 11,
    wherein the probe holder further comprises a plurality of doors,
    wherein each door is configured to secure one or more needle-like instruments among the plurality of needle-like instruments.

13. The medical guidance apparatus according to claim 12,
    wherein the probe holder further comprises a plurality of adjusting mechanisms,
    wherein each adjusting mechanism is configured to hold one of the plurality of doors with respect to the probe holder with an adjustable holding force, and wherein each pair of a door and a adjusting mechanism is configured to secure the one or more needle-like instruments at an angle with respect to the axis of the rotatable ring.

14. The medical guidance apparatus according to claim 1, further comprising:
an adhesive marker attached to an underside surface of the base assembly,
wherein the adhesive marker comprises a backing material and an adhesive extending across an underside surface of the backing material, and
wherein the backing material comprises a peel-away portion aligned with the opening of the base assembly.

15. The medical guidance apparatus according to claim 14, wherein the adhesive marker further comprises a center marker disposed on the peel-away portion, and wherein the center marker indicates a center point of the opening.

16. The medical guidance apparatus according to claim 1, wherein
the base assembly has top and bottom surfaces and the opening connects the top and bottom surfaces;
the rotatable ring is attached to the top surface of the base assembly;
the first end of the removable arc member is pivotably connected to a first section of the rotatable ring, and the second end of the removable arc member is releasably attached to a second section diametrically opposite to the first section of the rotatable ring, and
the probe holder is mounted on the removable arc member so as to hold the needle-like instrument at a desired angle relative to the axis of the rotatable ring.

17. The medical guidance apparatus according to claim 16, wherein the first end of the removable arc member includes a c-shaped clip which is pivotably hinged to a cylindrical pin arranged in an arc hinge section of the rotatable ring.

18. The medical guidance apparatus according to claim 17, wherein the c-shaped clip is rotatable around the cylindrical pin such that the removable arc member is privotable relative to the rotatable ring.

19. The medical guidance apparatus according to claim 18, wherein, in a configuration where the removable arc member is pivoted relative to the rotatable ring, the removable arc member is removable from rotatable ring by disengaging the c-shaped clip from the cylindrical pin.

20. The medical guidance apparatus according to claim 18, wherein, in a configuration where the removable arc member is pivoted relative to the rotatable ring, the first end and the second end of the removable arc member are disposed at a right angle or greater with respect to the plane of the rotatable ring, such that the removable arc member and the probe holder do not interfere with the opening of the base assembly.

21. The medical guidance apparatus according to claim 18, wherein a length of the c-shaped clip along the circumference of the rotatable ring is greater than a thickness of the removable arc member.

22. The medical guidance apparatus according to claim 16, wherein the second end of the removable arc member includes a latch locking mechanism which is releasably clipped onto an arc support section of the rotatable ring.

23. The medical guidance apparatus according to claim 22,
wherein the latch locking mechanism includes a snap joint having a protruding part, and the arc support section includes an undercut opening, and
wherein, during an operation of joining the second end of the removable arc member to the rotatable ring, the latching mechanism exerts a deflecting force on the snap joint and the protruding part catches or engages the undercut opening.

24. The medical guidance apparatus according to claim 23,
wherein the deflecting force is exerted in a direction from the second end towards the first end of the removable arch member, and
wherein a needle-like instrument mounted on the probe holder exerts a force substantially perpendicular to the direction of the deflecting force.

25. The medical guidance apparatus according to claim 16,
wherein the probe holder is configured to move along an arcuate path corresponding to a shape of the removable arc member, and
wherein the probe holder is configured to be fixed at any given position along the removable arc member using a cam latch mechanism to direct the needle-like instrument at the desired angle relative to the axis of the rotatable ring.

26. The medical guidance apparatus according to claim 16, further comprising:
a rotary encoder configured to measure a rotational position of the rotatable ring with respect to the base assembly; and
a circuit board configure to receive from the rotary encoder electric signals corresponding the rotational positon of the rotatable ring,
wherein the rotary encoder and the circuit board are arranged on the base plate and are covered at least partially by a housing of the rotatable ring.

27. The medical guidance apparatus according to claim 1, wherein
the first end of the removable arc member is releasably attached to the rotatable ring and the second end of the removable arc member is not attached to the rotatable ring but extends to a plane of the axis of the rotatable ring; and
the probe holder is mounted on the removable arc member so as to hold a needle-like instrument at a desired angle relative to the base plate such that an insertion path of the needle-like instrument intersects the axis of the cylindrical opening at the bottom surface of the base plate.

28. The medical guidance apparatus according to claim 1, wherein, in the configuration where the guide is mated with the base assembly, the removable arc member is configured to be partially or fully removed from the rotatable ring.

29. The medical guidance apparatus according to claim 1, wherein, in a configuration where the needle-like instrument is inserted into the subject, the removable arc member is partially or completely removable from the rotatable ring, while the needle-like instrument remains inserted into the subject.

* * * * *